United States Patent
Høgset et al.

(10) Patent No.: US 10,537,639 B2
(45) Date of Patent: Jan. 21, 2020

(54) COMPOUND AND METHOD

(71) Applicant: PCI Biotech AS, Oslo (NO)

(72) Inventors: Anders Høgset, Oslo (NO); Pål Johansen, Winterthur (CH)

(73) Assignee: PCI BIOTECH AS, Oslo (NO)

( * ) Notice: Subject to any disclaimer, the term of this patent is extended or adjusted under 35 U.S.C. 154(b) by 0 days.

(21) Appl. No.: 15/506,453

(22) PCT Filed: Aug. 28, 2015

(86) PCT No.: PCT/EP2015/069794
§ 371 (c)(1),
(2) Date: Feb. 24, 2017

(87) PCT Pub. No.: WO2016/030529
PCT Pub. Date: Mar. 3, 2016

(65) Prior Publication Data
US 2017/0252441 A1  Sep. 7, 2017

(30) Foreign Application Priority Data

Aug. 28, 2014 (GB) .................................. 1415247.4
Nov. 21, 2014 (GB) .................................. 1420773.2

(51) Int. Cl.
*A61K 41/00* (2006.01)
*A61K 47/54* (2017.01)

(52) U.S. Cl.
CPC ................................ *A61K 41/0042* (2013.01)

(58) Field of Classification Search
None
See application file for complete search history.

(56) References Cited

FOREIGN PATENT DOCUMENTS

| JP | 2004-520823 | 7/2004 |
|---|---|---|
| JP | 2007-510759 | 4/2007 |
| JP | 2011-522837 | 8/2011 |
| WO | 96/07432 | 3/1996 |
| WO | 00/54802 | 9/2000 |
| WO | 02/44396 | 6/2002 |
| WO | 02/48167 | 6/2002 |
| WO | 03/020309 | 3/2003 |
| WO | 2005/046622 | 5/2005 |
| WO | 2005/097976 | 10/2005 |
| WO | 2009/149397 | 12/2009 |
| WO | 2011/011797 | 1/2011 |
| WO | 2013/189663 | 12/2013 |
| WO | 2014/139597 | 9/2014 |
| WO | 2015/028574 | 3/2015 |
| WO | 2015/028575 | 3/2015 |
| WO | 2015/154832 | 10/2015 |

OTHER PUBLICATIONS

Stern, Peter L. Therapy of Human Papillomavirus-Related Disease. Vaccine. 2012, 30(05): F71-F82.*
Håkerud et al., "Intradermal photosensitisation facilitates stimulation of MHC class-I restricted CD8 T-cell responses of co-administered antigen", Journal of Controlled Release, 174: 143-150 (2014).
Waeckerle-Men et al., "Photochemical targeting of antigens to the cytosol for stimulation of MHC class-I-restricted T-cell responses", European Journal of Pharmaceutics and Biopharmaceutics, 85(1): 34-41 (2013).
Clive et al., "Use of GM-CSF as an adjuvant with cancer vaccines: beneficial or detrimental?", Expert Review of Vaccines, 9(5): 519-525 (2010).
International Search Report and Written Opinion of the International Searching Authority, dated Nov. 30, 2015 in corresponding International Application No. PCT/EP2015/069794.
Mukherjee et al., "Dendritic cells infected with a vaccinia virus interleukin-2 vector secrete high levels of IL-2 and can become efficient antigen presenting cells that secrete high levels of the immunostimulatory cytokine IL-12", Cancer Gene Therapy, 10: 591-602 (2003).
Girolomoni et al., "Establishment of a cell line with features of early dendritic cell precursors from fetal mouse skin", Eur. J. Immunol. 25: 2163-2169 (1995).
Arico et al., "Interferon-α as Antiviral and Antitumor Vaccine Adjuvants: Mechanisms of Action and Response Signature", J. Interferon Cytokine Res. 32(6): 235-247 (2012).
Capitini et al., "Cytokines as Adjuvants for Vaccine and Cellular Therapies for Cancer", American Journal of Immunology, 5(3): 65-83 (2009).
Parmiani et al., "Opposite immune functions of GM-CSF administered as vaccine adjuvant in cancer patients", Annals of Oncology, 18, 226-232 (2007).
Office Action and Search Report, dated Apr. 30, 2014 in corresponding GB patent application No. GB 1315296.2.
Notification of Reasons for Rejection dated Jul. 9, 2019 in corresponding Japanese Patent Application No. 2017-511702 with English translation.

* cited by examiner

*Primary Examiner* — Samantha L Shterengarts
(74) *Attorney, Agent, or Firm* — Wenderoth, Lind & Ponack, L.L.P.

(57) ABSTRACT

The present invention provides a method of expressing an antigenic molecule or a part thereof on the surface of a cell using a photochemical internalization method in which a cytokine, preferably GM-CSF, is used to enhance the method. The method may be used to stimulate an immune response and for various therapeutic or prophylactic methods. Pharmaceutical compositions or kits comprising the components for use in the method, cells produced by the method and their use in therapy and prophylaxis also form aspects of the invention.

Figure 1A:
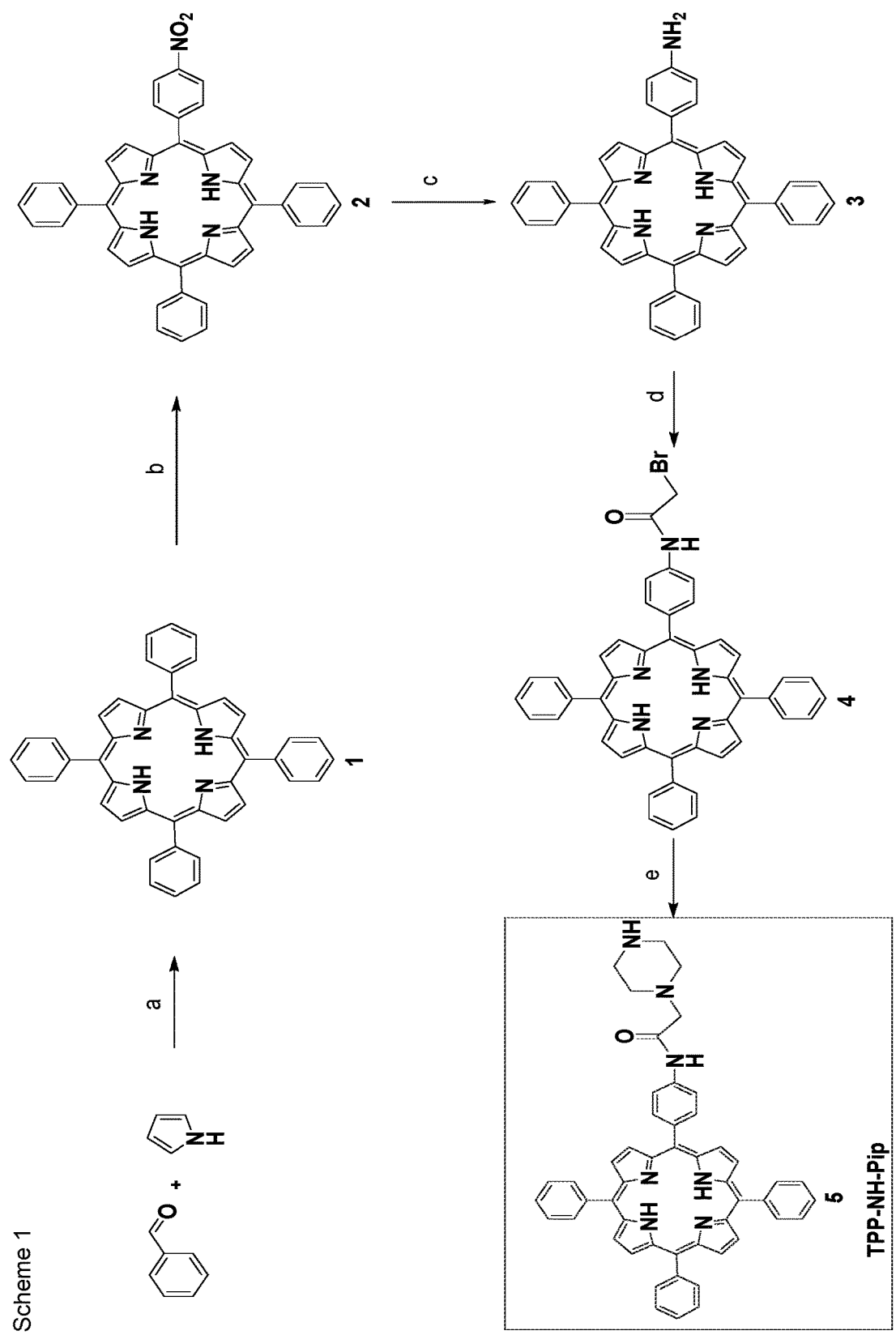

28 Claims, 8 Drawing Sheets
Specification includes a Sequence Listing.

Scheme 1

Scheme 2

Scheme 3

Scheme 4

A

B

Compound 26 is a mixture of inseparable isomers. Here and onwards only one of the possible isomers is shown.

28
TPC-CO-pip

Scheme 5A

Scheme 5B

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence

```
<220> FEATURE:
<223> OTHER INFORMATION: antigen epitope

<400> SEQUENCE: 1

Ser Ile Ile Asn Phe Glu Lys Leu
1               5

<210> SEQ ID NO 2
<211> LENGTH: 34
<212> TYPE: PRT
<213> ORGANISM: Artificial Sequence
<220> FEATURE:
<223> OTHER INFORMATION: synthetic peptide

<400> SEQUENCE: 2

Gln Ala Glu Pro Asp Arg Ala His Tyr Asn Ile Val Thr Phe Cys Cys
1               5                   10                  15

Lys Cys Asp Ser Thr Leu Arg Leu Cys Val Gln Ser Thr His Val Asp
                20                  25                  30

Ile Arg
```

COMPOUND AND METHOD

The present invention relates to a method of vaccination or immunisation involving the use of a photosensitizing agent, an antigenic molecule, e.g. a vaccine component, and an agent which enhances the effect of photochemical internalization (PCI)-mediated vaccination which is a cytokine as defined herein, and irradiation with light of a wavelength effective to activate the photosensitizing agent. The invention also relates to antigenic, e.g. vaccine compositions, useful in such a method. The invention also provides a method of generating antigen presenting cells which may be used to generate an immune response, e.g. for vaccination, which involves using the same components as above to introduce antigenic molecules, e.g. vaccine components, into cells to achieve antigen presentation, and to antigenic compositions useful in such a method. The invention also provides use of cells generated in vitro by such methods for administration to a patient in vivo to elicit an immune response, e.g. to achieve vaccination. A method of internalising an antigenic molecule into a cell is also provided.

Vaccination involves administration of antigenic molecules to provoke the immune system to stimulate development of an adaptive immunity to a pathogen. Vaccines can prevent or improve morbidity from infection. Vaccination is the most effective method of preventing infectious diseases, and widespread immunity due to vaccination is largely responsible for the worldwide eradication of smallpox and the restriction of diseases such as polio, measles, and tetanus from much of the world.

The active agent of a vaccine may be intact but inactivated (non-infective) or attenuated (with reduced infectivity) forms of the causative pathogens, or purified components of the pathogen that have been found to be immunogenic (e.g., outer coat proteins of a virus). Toxoids are produced for immunization against toxin-based diseases, such as the modification of tetanospasmin toxin of tetanus to remove its toxic effect but retain its immunogenic effect.

Since most vaccines are taken up by antigen presenting cells through endocytosis and transported via endosomes to lysosomes for antigen digestion and presentation via the MHC class-II pathway, vaccination primarily activates CD4 T-helper cells and B cells. To combat disorders or diseases such as cancer, as well as intracellular infections, the stimulation of cytotoxic CD8 T-cell responses is important. However, the induction of cytotoxic CD8 T cells usually fails due to the difficulty in delivering antigen to the cytosol and to the MHC class-I pathway of antigen presentation. Photochemical internalisation (PCI) improves delivery of molecules into the cytosol and methods of vaccination which employ PCI are known. PCI is a technique which uses a photosensitizing agent, in combination with an irradiation step to activate that agent, and is known to achieve release of molecules co-administered to a cell into the cell's cytosol. This technique allows molecules that are taken up by the cell into organelles, such as endosomes, to be released from these organelles into the cytosol, following irradiation. PCI provides a mechanism for introducing otherwise membrane-impermeable (or poorly permeable) molecules into the cytosol of a cell in a manner which does not result in widespread cell destruction or cell death.

The basic method of photochemical internalisation (PCI), is described in WO 96/07432 and WO 00/54802, which are incorporated herein by reference. In such methods, the molecule to be internalised (which in the present invention would be the antigenic molecule), and a photosensitizing agent are brought into contact with a cell. The photosensitizing agent and the molecule to be internalised are taken up into a cellular membrane-bound subcompartment within the cell, i.e. they are endocytosed into an intracellular vesicle (e.g. a lysosome or endosome). On exposure of the cell to light of the appropriate wavelength, the photosensitizing agent is activated which directly or indirectly generates reactive species which disrupt the intracellular vesicle's membranes. This allows the internalized molecule to be released into the cytosol.

It was found that in such a method the functionality or the viability of the majority of the cells was not deleteriously affected. Thus, the utility of such a method, termed "photochemical internalisation" was proposed for transporting a variety of different molecules, including therapeutic agents, into the cytosol i.e. into the interior of a cell.

WO 00/54802 utilises such a general method to present or express transfer molecules on a cell surface. Thus, following transport and release of a molecule into the cell cytosol, it (or a part of that molecule) may be transported to the surface of the cell where it may be presented on the outside of the cell i.e. on the cell surface. Such a method has particular utility in the field of vaccination, where vaccine components i.e. antigens or immunogens, may be introduced to a cell for presentation on the surface of that cell, in order to induce, facilitate or augment an immune response.

Whilst vaccination has achieved some noteworthy successes, there remains a need for alternative and improved vaccination methods. The present invention addresses this need.

The present inventors have surprisingly found that, advantageously, a method involving the use of a photosensitizing agent, an antigenic molecule, e.g. a vaccine component, and an agent which is a cytokine as defined herein, and irradiation with light of a wavelength effective to activate the photosensitizing agent results in improved vaccination or an improved immune response.

As will be described in more detail in the Examples below, the method of the invention provides improved vaccination or an improved immune response, e.g. production of an increased amount of antigen-specific T cells. It is expected that synergistic effects are achieved.

Whilst not wishing to be bound by theory, it is believed that the methods of the invention result in increased antigen presentation on MHC Class I molecules leading to an increased CD8+ T cell responses and hence improved vaccination methods. As disclosed in the Examples a model system employing OT-1 cells can be used for assessing MHC class I presentation (see e.g. Delamarre et al. J. Exp. Med. 198:111-122, 2003). In this model system MHC class I presentation of the antigen epitope SIINFEKL leads to activation of the OT-1 T-cells, and the activation can be measured as an increase in proliferation of the antigen-specific T-cells or increased production of IFNγ or IL-2.

Thus, in a first aspect the present invention provides a method of expressing an antigenic molecule or a part thereof on the surface of a cell, comprising contacting said cell with said antigenic molecule, a photosensitizing agent, and an agent which is a cytokine, and irradiating the cell with light of a wavelength effective to activate the photosensitising agent, wherein said antigenic molecule is released into the cytosol of the cell and the antigenic molecule or a part thereof is subsequently presented on the cell's surface.

Preferably this method (and subsequently described methods) employ only the above described three active ingredients (agents) in said method and the agents are present at appropriate levels (e.g. at the minimum levels described below) in the methods such that they affect the efficacy of the method (i.e. have an active role in enhancing PCI vaccination/antigen presentation/immune response stimulation). Thus preferably the agents are present in buffers with no other active ingredients.

In such methods said antigenic molecule and said photosensitizing agent, and optionally said agent which is a cytokine as defined herein, are each taken up into an intracellular vesicle; and when the cell is irradiated the membrane of the intracellular vesicle is disrupted releasing the antigenic molecule into the cytosol of the cell.

The various agents may be taken up into the same or a different intracellular vesicle relative to each other. It has been found that active species produced by photosensitizers may extend beyond the vesicle in which they are contained and/or that vesicles may coalesce allowing the contents of a vesicle to be released by coalescing with a disrupted vesicle. As referred to herein "taken up" signifies that the molecule taken up is wholly contained within the vesicle. The intracellular vesicle is bounded by membranes and may be any such vesicle resulting after endocytosis, e.g. an endosome or lysosome.

As used herein, a "disrupted" compartment refers to destruction of the integrity of the membrane of that compartment either permanently or temporarily, sufficient to allow release of the antigenic molecule contained within it.

A "photosensitizing agent" as referred to herein is a compound that is capable of translating the energy of absorbed light into chemical reactions when the agent is activated on illumination at an appropriate wavelength and intensity to generate an activated species. The highly reactive end products of these processes can result in cyto- and vascular toxicity. Conveniently such a photosensitizing agent may be one which localises to intracellular compartments, particularly endosomes or lysosomes.

Photosensitisers may exert their effects by a variety of mechanisms, directly or indirectly. Thus for example, certain photosensitisers become directly toxic when activated by light, whereas others act to generate toxic species, e.g. oxidising agents such as singlet oxygen or other reactive oxygen species, which are extremely destructive to cellular material and biomolecules such as lipids, proteins and nucleic acids.

A range of such photosensitizing agents are known in the art and are described in the literature, including in WO96/07432, which is incorporated herein by reference, and may be used in method of the invention. There are many known photosensitising agents, including porphyrins, phthalocyanines, purpurins, chlorins, benzoporphyrins, lysomotropic weak bases, naphthalocyanines, cationic dyes and tetracyclines or derivatives thereof (Berg et al., (1997), J. Photochemistry and Photobiology, 65, 403-409). Other photosensitising agents include texaphyrins, pheophorbides, porphycenes, bacteriochlorins, ketochlorins, hematoporphyrin derivatives, and endogenous photosensitizers induced by 5-aminolevulinic acid and derivatives thereof, Photofrin, dimers or other conjugates between photosensitizers.

Porphyrins are the most extensively studied photosensitising agents. Their molecular structure includes four pyrrole rings linked together via methine bridges. They are natural compounds which are often capable of forming metal-complexes. For example in the case of the oxygen transport protein hemoglobin, an iron atom is introduced into the porphyrin core of heme B.

Chlorins are large heterocyclic aromatic rings consisting, at the core, of three pyrroles and one pyrroline coupled through four methine linkages. Unlike porphyrin, a chlorin is therefore largely aromatic, but not aromatic through the entire circumference of the ring.

The skilled man will appreciate which photosensitisers are suitable for use in the present invention. Particularly preferred are photosensitizing agents which locate to endosome or lysosomes of cells. Thus, the photosensitizing agent is preferably an agent which is taken up into the internal compartments of lysosomes or endosomes. Preferably the photosensitizing agent is taken up into intracellular compartments by endocytosis. Preferred photosensitisers are di- and tetrasulfonated aluminium phthalocyanine (e.g. AlPcS$_{2a}$), sulfonated tetraphenylporphines (TPPS$_n$), sulfonated tetraphenyl bacteriochlorins (e.g. TPBS$_{2a}$), nile blue, chlorin e$_6$ derivatives, uroporphyrin I, phylloerythrin, hematoporphyrin and methylene blue. Further appropriate photosensitizers for use in the invention are described in WO03/020309, which is also incorporated herein by reference, namely sulfonated meso-tetraphenyl chlorins, preferably TPCS$_{2a}$. Preferred photosensitizing agents are amphiphilic photosensitizers (e.g. disulfonated photosensitizers) such as amphiphilic phthalocyanines, porphyrins, chlorins and/or bacteriochlorins, and in particular include TPPS$_{2a}$ (tetraphenylporphine disulfonate), AlPcS$_{2a}$ (aluminium phthalocyanine disulfonate), TPCS$_{2a}$ (tetraphenyl chlorin disulfonate) and TPBS$_{2a}$ (tetraphenyl bacteriochlorin disulfonate), or pharmaceutically acceptable salts thereof. Also preferred are hydrophilic photosensitizing agents, for example TPPS$_4$ (meso-tetraphenylporphine tetrasulfonate). Particularly preferred photosensitizing agents are sulfonated aluminium phthalocyanines, sulfonated tetraphenylporphines, sulfonated tetraphenylchlorins and sulfonated tetraphenylbacteriochlorins, preferably TPCS$_{2a}$, AlPcS$_{2a}$, TPPS$_4$ and TPBS$_{2a}$. In a particularly preferred embodiment of the present invention the photosensitizing agent is the chlorin TPCS$_{2a}$ (Disulfonated tetraphenyl chlorin, e.g. Amphinex®).

A photosensitiser may be linked to a carrier to provide the photosensitising agent. Thus, in a preferred aspect of this embodiment of the invention the photosensitising agent is a conjugate of a photosensitiser and chitosan as defined in formula (I):

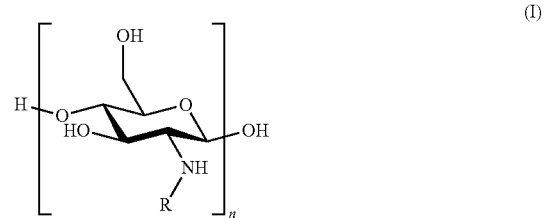

(I)

wherein
n is an integer greater than or equal to 3;
R appears n times in said compound, and
in 0.1%-99.9% (preferably 0.5%-99.5%) of said total Rn groups, each R is a group A selected from:

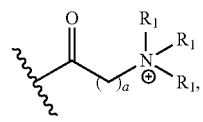

wherein each $R_1$, which may be the same or different, is selected from H, $CH_3$ and $-(CH_2)_b-CH_3$; a is 1, 2, 3, 4 or 5; and b is 0, 1, 2, 3, 4 or 5 (in which the counter-ion may be, for example, $Cl^-$); preferably $R_1$, is $CH_3$ and b is 1, and

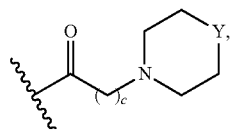

wherein Y is O; S; $SO_2$; $-NCH_3$; or $-N(CH_2)_dCH_3$, c=1, 2, 3, 4 or 5; and d=1, 2, 3, 4 or 5, preferably Y is $NCH_3$ and c is 1, wherein each R group may be the same or different, and in 0.1%-99.9% (preferably 0.5%-99.5%) of said total Rn groups, each R is a group B selected from:

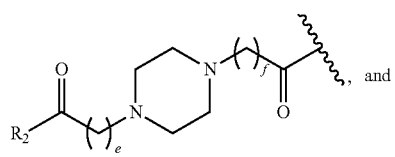, and

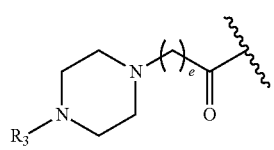

wherein
e is 0, 1, 2, 3, 4 or 5; and f is 1, 2, 3, 4 or 5; preferably e and f=1, $R_2$ is a group selected from:

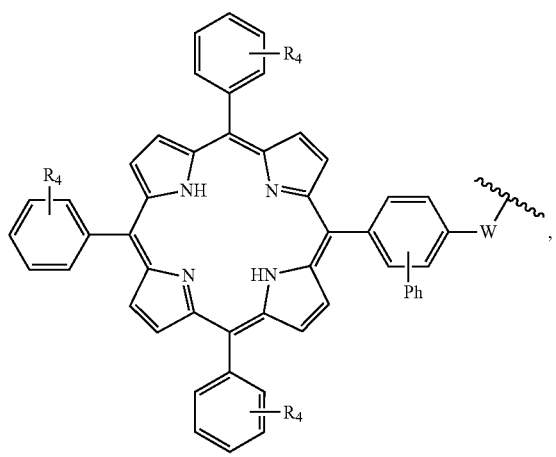

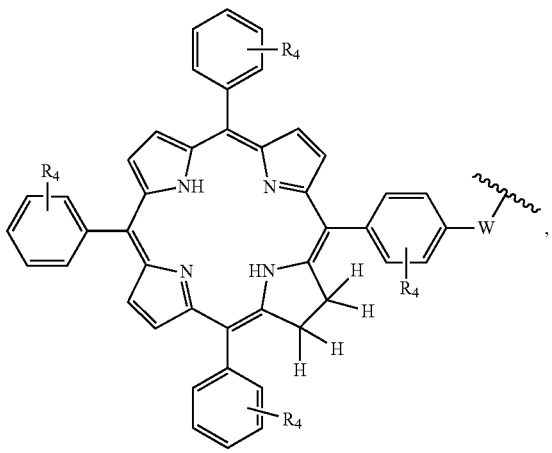
and

W is a group selected from O, S, NH or $N(CH_3)$; preferably NH, $R_3$ is a group selected from:

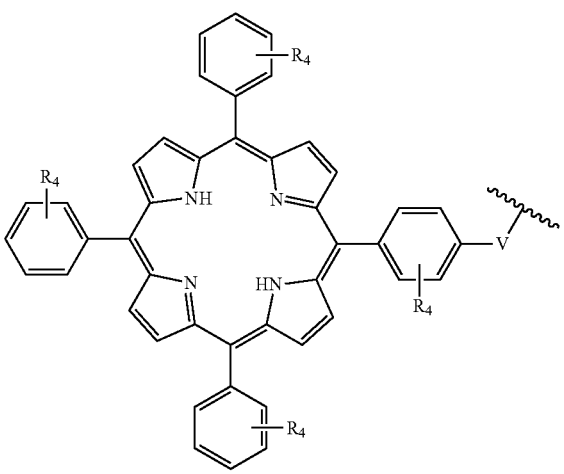

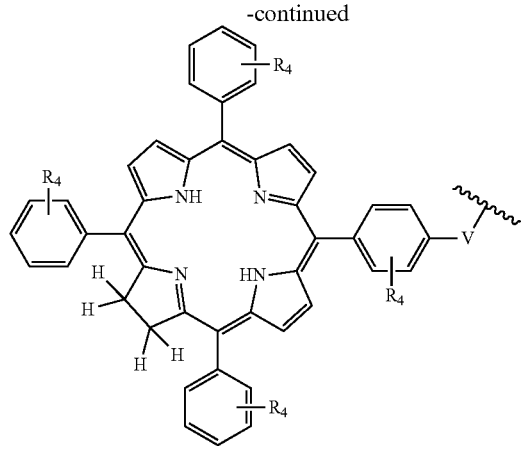

, and

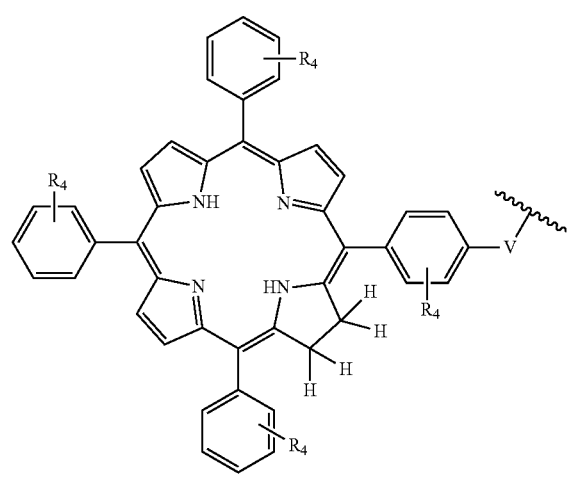

,

V is a group selected from CO, SO$_2$, PO, PO$_2$H or CH$_2$; preferably CO, and R$_4$ is a group (substituted in the o, m or p position), which may be the same or different, selected from H, —OH, —OCH$_3$, —CH$_3$, —COCH$_3$, C(CH$_3$)$_4$, —NH$_2$, —NHCH$_3$, —N(CH$_3$)$_2$ and —NCOCH$_3$, preferably H, wherein each R group may be the same or different.

The chitosan polymer has at least 3 units (n=3). However, preferably n is at least 10, 20, 50, 100, 500, 1000 e.g. from 10 to 100 or 10 to 50.

In a preferred embodiment R$_2$ is selected from

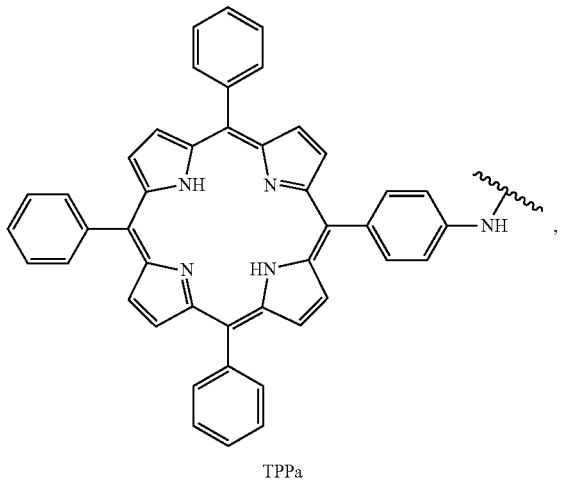

TPPa

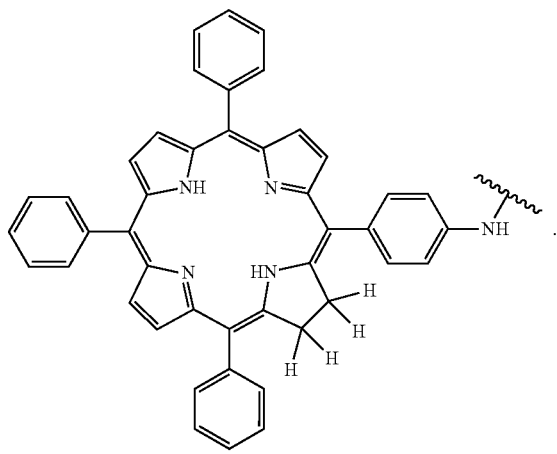

TPCa$_1$

, and

TPCa$_2$

.

In a further preferred embodiment R₃ is selected from
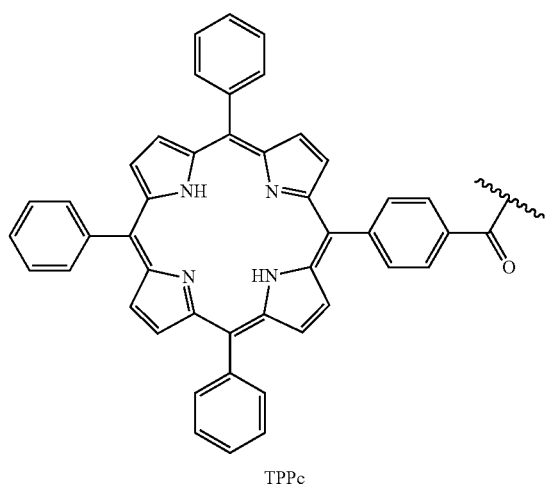
TPPc
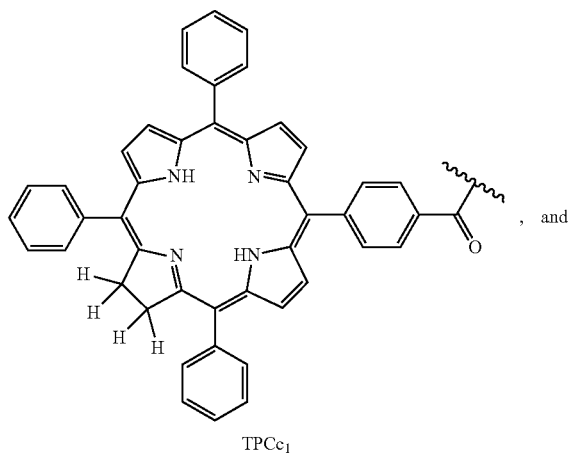
TPCc₁
, and
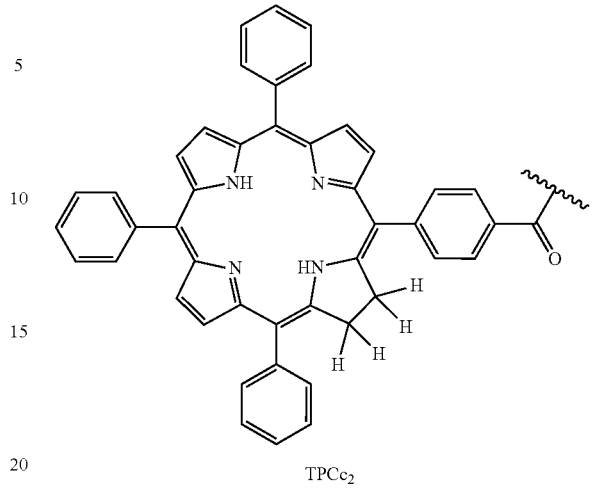
TPCc₂
Preferably $R_2$ or $R_3$ is $TPP_a$, $TPC_{a1}$ or $TPC_{c1}$.
Group A may provide 70 to 95% of the total Rn groups and group B may provide 5 to 30% of the total Rn groups.
In a most preferred embodiment the conjugate of a photosensitiser and chitosan is selected from (see numbering in Schemes 1-5B in FIG. 4):
17: B: 25%, A: 75%
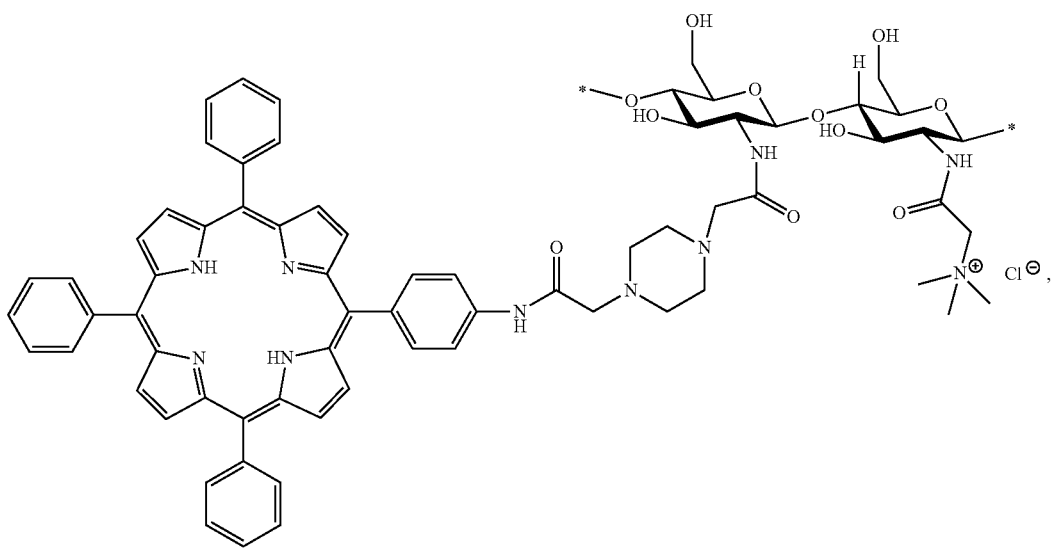

19: B: 25%, A: 75%
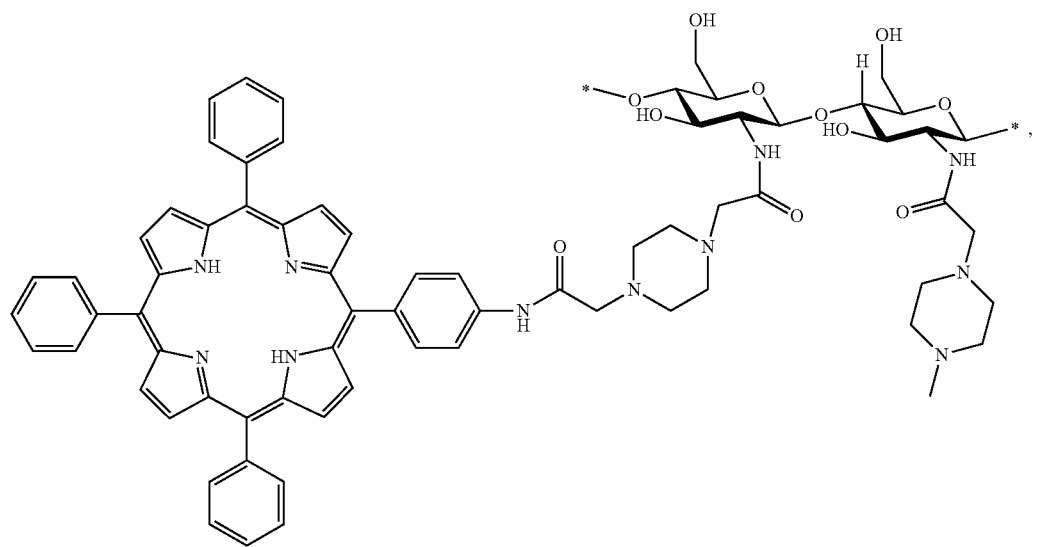
33: B: 10%; A: 90%
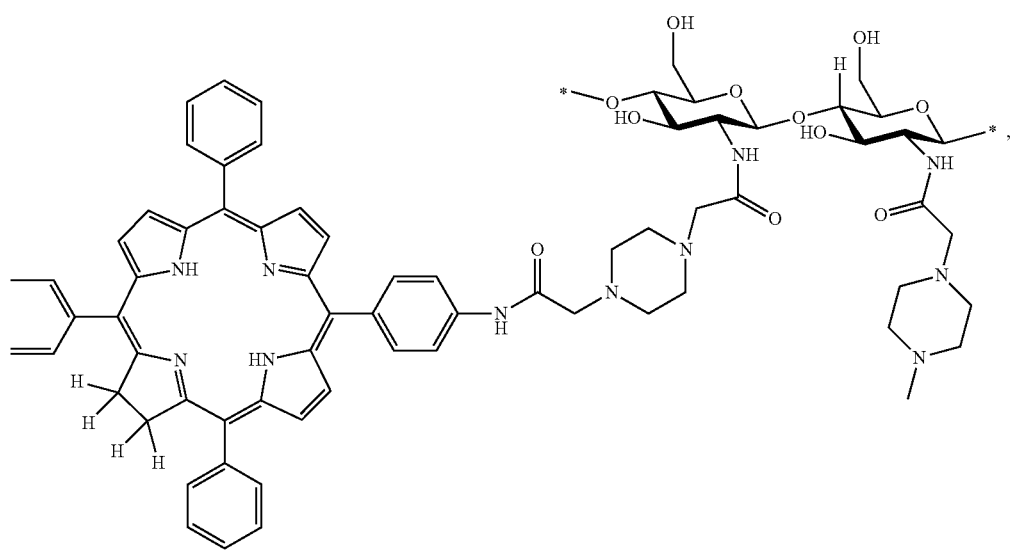

and

37: B: 10%; A: 90%

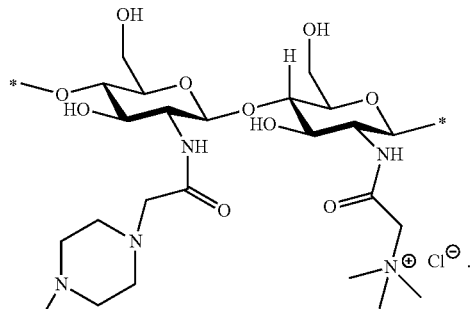

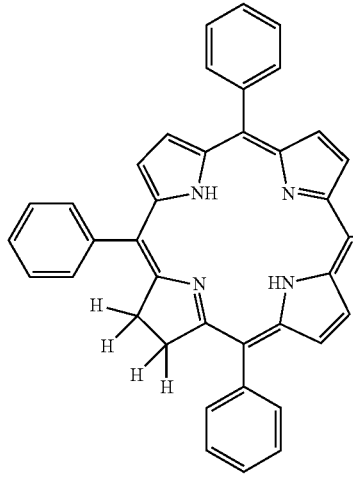

In the above structures, the A/B % values provided refer to the proportion of Rn groups which are group A or B. The asterisks denote the remainder of the chitosan polymer.

These compounds may be made by synthesis methods which utilise procedures standard in the art, which will be familiar to the skilled man. By way of example, synthesis of the preferred conjugates discussed below, numbers 17, 19, 33 and 37, is shown in reaction schemes 1-5B in FIG. 1 (and see also FIG. 1 legend).

An "antigenic" molecule as referred to herein is a molecule which itself, or a part thereof, is capable of stimulating an immune response, when presented to the immune system or immune cells in an appropriate manner. Advantageously, therefore the antigenic molecule will be a vaccine antigen or vaccine component, such as a polypeptide containing entity.

Many such antigens or antigenic vaccine components are known in the art and include all manner of bacterial or viral antigens or indeed antigens or antigenic components of any pathogenic species including protozoa or higher organisms. Whilst traditionally the antigenic components of vaccines have comprised whole organisms (whether live, dead or attenuated) i.e. whole cell vaccines, in addition sub-unit vaccines, i.e. vaccines based on particular antigenic components of organisms e.g. proteins or peptides, or even carbohydrates, have been widely investigated and reported in the literature. Any such "sub-unit"-based vaccine component may be used as the antigenic molecule of the present invention.

However, the invention finds particular utility in the field of peptide vaccines. Thus, a preferred antigenic molecule according to the invention is a peptide (which is defined herein to include peptides of both shorter and longer lengths i.e. peptides, oligopeptides or polypeptides, and also protein molecules or fragments thereof e.g. peptides of 5-500 e.g. 10 to 250 such as 15 to 75, or 8 to 25 amino acids). The invention has been illustrated using, for example, ovalbumin as the antigenic molecule which forms a preferred aspect of the invention, but antigenic molecules which are not ovalbumin are particularly preferred, such as those used in the Examples.

A vast number of peptide vaccine candidates have been proposed in the literature, for example in the treatment of viral diseases and infections such as AIDS/HIV infection or influenza, canine parvovirus, bovine leukaemia virus, hepatitis, etc. (see e.g. Phanuphak et al., Asian Pac. J. Allergy. Immunol. 1997, 15(1), 41-8; Naruse, Hokkaido Igaku Zasshi 1994, 69(4), 811-20; Casal et al., J. Virol., 1995, 69(11), 7274-7; Belyakov et al., Proc. Natl. Acad. Sci. USA, 1998, 95(4), 1709-14; Naruse et al., Proc. Natl. Sci. USA, 1994 91(20), 9588-92; Kabeya et al., Vaccine 1996, 14(12), 1118-22; Itoh et al., Proc. Natl. Acad. Sci. USA, 1986, 83(23) 9174-8. Similarly bacterial peptides may be used, as indeed may peptide antigens derived from other organisms or species.

In addition to antigens derived from pathogenic organisms, peptides have also been proposed for use as vaccines against cancer or other diseases such as multiple sclerosis. For example, mutant oncogene peptides hold great promise as cancer vaccines acting as antigens in the stimulation of cytotoxic T-lymphocytes. (Schirrmacher, Journal of Cancer Research and Clinical Oncology 1995, 121, 443-451; Curtis Cancer Chemotherapy and Biological Response Modifiers, 1997, 17, 316-327). Thus a melanoma antigen may be used as the antigenic molecule of the invention. In alternative embodiments, an antigenic molecule which is not a melanoma antigen may be used. A "melanoma antigen" as referred to herein is a molecule derived from a melanoma cell which itself, or a part thereof, is capable of stimulating an immune response, when presented to the immune system or immune cells in an appropriate manner. A molecule "derived" from a melanoma is a molecule which may appear in the melanoma cell or which is modified relative to the native molecule in the melanoma, e.g. by truncation, post-expression modification and/or sequence modification providing the modified molecule retains one or more epitopes from the native molecule which allows the modified molecule to generate an immune response which would recognise the native molecule. The melanoma antigen may be obtained by isolation from appropriate sources e.g. the subject's melanoma or may be synthesised e.g. by chemical synthesis or peptide/protein expression.

A synthetic peptide vaccine has also been evaluated for the treatment of metastatic melanoma (Rosenberg et al., Nat. Med. 1998, 4(3), 321-7). A T-cell receptor peptide vaccine for the treatment of multiple sclerosis is described in Wilson et al., J. Neuroimmunol. 1997, 76(1-2), 15-28. Any such peptide vaccine component may be used as the antigenic molecule of the invention, as indeed may any of the peptides described or proposed as peptide vaccines in the literature. The peptide may thus be synthetic or isolated or otherwise derived from an organism. Preferred peptides include those used in the Examples, e.g. a HPV peptide such as the HPV long peptide having the sequence QAEPDRAHYNIVTFC-CKCDSTLRLCVQSTHVDIR.

In one embodiment an adjuvant is also used in the methods of the invention. For example, the adjuvant may be selected from a Toll-like receptor (TLR) ligand, such as a TLR 3 ligand, for example Poly(IC) (e.g. high (e.g. average size of 1.5-8 kb) or low (e.g. average size of 0.2-1 kb) MW Poly(IC)). The dose of Poly(IC) may be between 5 μg and 200 μg, for example between 10 μg and 100 μg, preferably 10 μg or 50 μg for mice, which may be appropriately scaled where necessary for treatment of other animals. Products, methods or uses of the invention preferably contain or use Poly(IC).

Once released in the cell cytosol by the photochemical internalisation process, the antigenic molecule may be processed by the antigen-processing machinery of the cell. Thus, the antigenic molecule expressed or presented on the surface of the cell may be a part or fragment of the antigenic molecule which is internalised (endocytosed). A "part" of an antigenic molecule which is presented or expressed preferably comprises a part which is generated by antigen-processing machinery within the cell. Parts may, however, be generated by other means which may be achieved through appropriate antigen design (e.g. pH sensitive bonds) or through other cell processing means. Conveniently such parts are of sufficient size to generate an immune response, e.g. in the case of peptides greater than 5, e.g. greater than 10 or 20 amino acids in size.

As discussed herein, the agent which enhances PCI-mediated vaccination is a cytokine. The term "cytokine" encompasses a large and diverse family of regulators produced throughout the body by cells of a variety of embryological origin. Cytokines are small cell signaling molecules which can be proteins, peptides, or glycoproteins. Cytokines include immunomodulating agents, such as interleukins (IL) and interferons (IFN) and also colony stimulating factors, tumour necrosis factors (TNF) and other regulatory molecules. Cytokines have been classed as lymphokines, interleukins, and chemokines, based on their function, cell of secretion, or target of action. Each cytokine has a matching cell-surface receptor, which initiates cascades of intracellular signalling which alter cell functions. Cytokines are well known in the art and all such cytokines are encompassed for use according to the invention. Preferred families are as described herein.

Cytokines have been classified in various ways according to structure and/or function, and various families have been identified. The cytokines may be classified by virtue of the receptors to which they bind. The receptors (and hence their ligands) may be classified into Type 1 cytokine (hemopoietin) receptors, Type II cytokine receptors, TNF receptors, immunoglobulin superfamily receptors and seven transmembrane α-helical receptors.

Granulocyte-macrophage colony-stimulating factor (GM-CSF), along with C-CSF, M-CSF, IL-3 and IL-5, belongs to the family of cytokines which are ligands for hematopoietic cytokine receptors discussed above. Within this family of receptors is the GM-CSF receptor family, which have a common β chain. GM-CSF is secreted as a single chain glycoprotein containing 128 amino acids with a conserved di-sulphide bond by a variety of cell types. Functions of GM-CSF are mediated by the GM-CSF receptor, which comprises a GM-CSF-specific a chain and, in human cells, a β chain which is shared with the IL-3 and IL-5 receptors. The α chain is expressed as monomers on the cell surface, and binds to GM-CSF with high affinity. Following such binding, the β chain is recruited to the complex and activates signal transduction and functional responses. In addition, the α chain can exist as a soluble external molecule (generated by alternative splicing). This receptor competes with its membrane-bound counterpart for cytokine binding but does not participate in agonistic signalling. GM-CSF functions as a white blood cell growth factor. GM-CSF stimulates stem cells to produce granulocytes (neutrophils, eosinophils, and basophils) and monocytes. GM-CSF is therefore important in fighting infection.

Also within the type I cytokine receptor family is the IL-2 receptor family. Members of this family have a common γ chain. Receptors in this family include IL-2, IL-4, IL-7, IL-9, IL-15 and IL-21 receptors. The majority of interleukins are synthesized by helper CD4 T lymphocytes, as well as through monocytes, macrophages, and endothelial cells. They promote the development and differentiation of T, B, and hematopoietic cells.

IL-7, binds to the IL-7 receptor, which is a heterodimer consisting of Interleukin-7 receptor α and a common γ chain receptor. IL-7 is important for both B and T cell development. This cytokine and the hepatocyte growth factor (HGF) form a heterodimer that functions as a pre-pro-B cell growth-stimulating factor. IL-7 is also a cofactor for V(D)J rearrangement of the T cell receptor beta (TCRβ) during early T cell development. IL-7 can be produced locally by intestinal epithelial and epithelial goblet cells, but is not produced by lymphocytes themselves and serum IL-7 levels are inversely correlated with lymphocyte counts. Binding of the cytokine to its receptor results in signalling important for T-cell development, both within the thymus and survival within the periphery. IL-7 stimulates the differentiation of multipotent (pluripotent) hematopoietic stem cells into lymphoid progenitor cells (as opposed to myeloid progenitor cells where differentiation is stimulated by IL-3). It also stimulates proliferation of all cells in the lymphoid lineage (B cells, T cells and NK cells). It is important for proliferation during certain stages of B-cell maturation, T and NK cell survival, development and homeostasis.

As discussed above, IL-2, IL-15 and IL-21 are related to IL-7, in that they belong to the so-called gamma(c) family of cytokines, i.e. they bind to a receptor with a common γ chain. These cytokines all employ the common cytokine γ chain for signalling, and have potent effects on T-cells and NK cells.

IL-2 is produced mainly by T-helper cells and acts on a variety of immune cells of the innate and adaptive immune systems. IL-2 is a lymphokine that induces the proliferation of responsive T-cells. In addition, it acts on some B-cells, via receptor-specific binding, as a growth factor and as an antibody production stimulant. IL-2 is secreted as a single glycosylated polypeptide, and cleavage of a signal sequence is required for its activity. Solution NMR suggests that the structure of IL-2 comprises a bundle of 4 helices (termed A-D), flanked by 2 shorter helices and several poorly-defined loops. Residues in helix A, and in the loop region between helices A and B, are important for receptor binding. Secondary structure analysis has suggested similarity to IL-4 and GM-CSF.

IL-15 is constitutively expressed by a variety of cell types and tissues, but is mainly membrane-bound. IL-15 and IL-2 exhibit similar immune effects and share the IL-2 receptor subunits IL-2Rγ and IL-2Rγ(c), but each cytokine has a separate α receptor. IL-15 has a variety of biological functions, including stimulation and maintenance of cellular immune responses. IL-15 stimulates the proliferation of T-lymphocytes.

IL-21 is homologous to IL-15, but the receptor is comprised of a unique subunit designated IL-21Rα and the IL-2Rγ(c). IL-21 is produced by activated CD4$^+$ T helper cells, and NK T cells. All lymphocytes and dendritic cells have IL-21 receptors. Stimulation of the receptor by cytokine binding can lead to costimulation, activation and proliferation of CD8+ T cells, augmentation of NK cytotoxicity, an increase in CD40-driven B cell proliferation, differentiation and isotype switching, and promotion and differentiation of Th17 cells.

Interferons (IFNs) are examples of cytokines that bind to type II cytokine receptors. Interferons are proteins made and released by host cells in response to the presence of pathogens such as viruses, bacteria, parasites or tumor cells. They allow for communication between cells to trigger the protective defenses of the immune system that eradicate pathogens or tumours. Interferons can activate immune cells, such as natural killer cells and macrophages and they increase the ability of uninfected hosts to resist new infection by virus.

Approximately ten distinct IFNs have been identified in mammals (seven in humans). There are three IFN classes, delineated on the basis of the type of receptor through which they signal. All type I IFNs bind to a specific cell surface receptor complex known as the IFN-α receptor (IFNAR) that consists of IFNAR1 and IFNAR2 chains. The type I interferons present in humans are IFN-α, IFN-β and IFN-ω. Type II IFNs bind to IFNGR, which consists of IFNGR1 and IFNGR2 chains. In humans this is IFN-γ. Type III Interferons signal through a receptor complex consisting of IL10R2 and IFNLR1.

IFN-α proteins, are produced by leukocytes, and are mainly involved in innate immune responses against viral infection. There are 13 subtypes: IFNA1, IFNA2, IFNA4, IFNA5, IFNA6, IFNA7, IFNA8, IFNA10, IFNA13, IFNA14, IFNA16, IFNA17 and IFNA21. The genes for these IFN-α molecules are found together in a cluster on chromosome 9.

In accordance with the invention, the agent may be any cytokine. All known forms of the above-discussed cytokines can be used in the present invention, including also functionally equivalent variants, derivatives and fragments thereof. Thus the term "cytokine" as used herein includes amino acid sequence variants of known cytokine polypeptides, and fragments of a cytokine polypeptide, or derivative thereof, as long as such fragments, variants or derivatives are active, or "functional", i.e. retain at least one function or activity (e.g. biological activity) of the relevant cytokine. The cytokine may be a recombinant polypeptide, a synthetic polypeptide or may be isolated from a natural source. Suitable cytokines are commercially available and would be known to the skilled man, for example human cytokines are available from GenScript (Piscataway, N.J., USA).

The cytokine may be from any species (more particularly any vertebrate species), but preferably will be mammalian, and more preferably human.

Variants of cytokines may include, for example, different allelic variants as they appear in nature e.g. in other species or due to geographical variation etc. Functionally equivalent variants may also include polypeptides which incorporate one or more amino acid substitutions, or intrasequence or terminal deletions or additions to known sequences.

Functionally equivalent derivatives may include chemical modifications of the amino acid sequence, including for example the inclusion of chemically substituted or modified amino acid residues or PEGylated cytokines.

A derivative may also be a molecule which is a peptidomimetic of a cytokine polypeptide. In other words, it may be a molecule which is functionally equivalent or similar to a polypeptide and which can adopt a 3-D structure which is similar to its polypeptide counterpart, but which is not composed solely of amino acids linked by peptide bonds. Thus, a peptidomimetic may be composed of sub-units which are not amino acids but which are structurally and functionally similar to an amino acid. The backbone moiety of the subunit may differ from a standard amino acid, e.g. it may comprise one or more nitrogen atoms instead of one or more carbon atoms. A preferred class of peptidomimetic is a peptoid, i.e. an N-substituted glycine. Peptoids are closely related to their peptide counterparts but differ chemically in that their side chains are appended to nitrogen atoms along the backbone of the molecule, rather than to the α-carbons as they are in amino acids.

All such variants and derivatives are included provided they retain an activity of the relevant cytokine and enhance photochemical internalisation, according to the present invention, e.g. enhance PCI-mediated vaccination as assessed by the methodology described in the Examples.

It is known in the art to modify the sequences of proteins or peptides, whilst retaining activity and this may be achieved using techniques which are standard in the art e.g. random or site directed mutagenesis, cleavage and ligation of nucleic acids, chemical peptide synthesis etc.

Preferably, amino acid changes are of a minor nature, that is conservative amino acid substitutions that do not significantly affect the folding and/or activity of the protein; small deletions, typically of 1 to 30 amino acids; small amino- or carboxyl-terminal extensions; addition of a small linker peptide of up to about 20-25 residues; or a small extension that facilitates purification by changing net charge or another function, such as a poly-histidine tract, an antigenic epitope or a binding domain. Hence, N and/or C extensions to the protein or peptides are included in the definition. The lengths of each extended derivative may vary, for example, derivatives may be extended by up to 50, 30, 20, 10 or 5 amino acids.

Examples of conservative substitutions are within the group of basic amino acids (such as arginine, lysine and histidine), acidic amino acids (such as glutamine and asparagine), hydrophobic amino acids (such as leucine, isoleucine and valine), aromatic amino acids (such as phenylalanine, tryptophan and tyrosine) and small amino acids (such as glycine, alanine, threonine and methionine). The cytokine preferably has at least 50%, 60%, 70%, 80%, 90%, 95%, 96%, 97%, 98%, 99% or 100% sequence identity or similarity to the known amino acid sequences of the cytokines described herein. For example, amino acid sequences of preferred, known cytokines are shown in the Table below:

| Cytokine | NCBI Reference Sequence | UniProtKB/Swiss-Prot Reference |
|---|---|---|
| granulocyte-macrophage colony-stimulating factor precursor (Homo sapiens) | NP_000749.2 (144 amino acids) | P04141 (also known as CSF2) |
| interleukin-2 precursor (Homo sapiens) | NP_000577.2 (153 amino acids) | P60568 |
| interleukin-7 isoform 1 precursor (Homo sapiens) | NP_000871.1 (177 amino acids) | P13232 |
| interleukin-15 isoform 1 preproprotein (Homo sapiens) | NP_000576.1 (162 amino acids) | P40933 |
| interleukin-21 isoform 2 precursor (Homo sapiens) | NP_001193935.1 (153 amino acids) | Q9HBE4 |
| interferon alpha-1/13 precursor (Homo sapiens) | NP_076918.1 (189 amino acids) | P01562 (also known as IFNA1) |

The degree of identity between two nucleic acid and two amino acid sequences may be determined by means of computer programs known in the art such as GAP provided in the GCG program package (Needleman and Wunsch, 1970, Journal of Molecular Biology 48: 443-453). For the purposes of determining the degree of identity between 2 amino acid sequences, GAP can be used with the following settings: GAP creation penalty of 3.0 and GAP extension penalty of 0.1. Amino acid similarity may be measured using the Best Fit program of GCG Version 10 Software package from the University of Wisconsin. This program uses the local homology algorithm of Smith and Waterman with the default values: Gap creation penalty=8, Gap extension penalty=2, Average match=2.912, Average mismatch=2.03.

Preferably the cytokine for use according to the invention is a cytokine that is a ligand for a type I or type II cytokine receptor. Especially preferably, the cytokine is a ligand for an IL-2 receptor family member or a GM-CSF receptor family member or the cytokine is an interferon, preferably a type I IFN. In a particularly preferred embodiment of the present invention the cytokine is selected from GM-CSF, IL-7, IFN-α, IL-2, IL-15 or IL-21, or homologs or derivatives thereof, even more preferably the cytokine is selected from GM-CSF, IL-7 or IFN-α. Most preferably the cytokine is GM-CSF though the invention extends to the use of cytokines which are not GM-CSF. Preferably the cytokine is from a human source.

As defined herein, a "ligand" is a molecule which is able to bind to a receptor and initiate signalling through that receptor, or antagonise or agonise signalling through that receptor by the native ligand.

As used herein "expressing" or "presenting" refers to the presence of the antigenic molecule or a part thereof on the surface of said cell such that at least a portion of that molecule is exposed and accessible to the environment surrounding that cell, preferably such that an immune response may be generated to the presented molecule or part thereof. Expression on the "surface" may be achieved in which the molecule to be expressed is in contact with the cell membrane and/or components which may be present or caused to be present in that membrane.

The term "cell" is used herein to include all eukaryotic cells (including insect cells and fungal cells). Representative "cells" thus include all types of mammalian and non-mammalian animal cells (such as fish cells), plant cells, insect cells, fungal cells and protozoa. Preferably, however, the cells are mammalian, for example cells from cats, dogs, horses, donkeys, sheep, pigs, goats, cows, mice, rats, rabbits, guinea pigs, but most preferably from humans. The cell which is subjected to the methods, uses etc. of the invention may be any cell which is capable of expressing, or presenting on its surface a molecule which is administered or transported into its cytosol.

The cell is conveniently an immune cell i.e. a cell involved in the immune response. However, other cells may also present antigen to the immune system and these also fall within the scope of the invention. The cells according to the present invention are thus advantageously antigen-presenting cells as described hereinafter. The antigen-presenting cell may be involved in any aspect or "arm" of the immune response as defined herein.

The stimulation of cytotoxic cells requires antigens to be presented to the cell to be stimulated in a particular manner by the antigen-presenting cells, for example MHC Class I presentation (e.g. activation of $CD8^+$ cytotoxic T-cells requires MHC-1 antigen presentation). Antibody-producing cells may also be stimulated by presentation of antigen by the antigen-presenting cells.

Antigens may be taken up by antigen-presenting cells by endocytosis and degraded in the endocytic vesicles to peptides. These peptides may bind to MHC class II molecules in the endosomes and be transported to the cell surface where the peptide-MHC class II complex may be recognised by CD4+ T helper cells and induce an immune response. Alternatively, proteins in the cytosol may be degraded, e.g. by proteasomes and transported into endoplasmic reticulum by means of TAP (transporter associated with antigen presentation) where the peptides may bind to MHC class I molecules and be transported to the cell surface (Yewdell and Bennink, 1992, Adv. Immunol. 52: 1-123). If the peptide is of foreign antigen origin, the peptide-MHC class I complex will be recognised by CD8+ cytotoxic T-cells (CTLs). The CTLs will bind to the peptide-MHC (HLA) class I complex and thereby be activated, start to proliferate and form a clone of CTLs. The target cell and other target cells with the same peptide-MHC class I complex on the cells surface may be killed by the CTL clone. Immunity against the foreign antigen may be established if a sufficient amount of the antigen can be introduced into the cytosol (Yewdell and Bennink, 1992, supra; Rock, 1996, Immunology Today 17: 131-137). This is the basis for development of inter alia cancer vaccines. One of the largest practical problems is to introduce sufficient amounts of antigens (or parts of the antigen) into the cytosol. This may be solved according to the present invention.

As mentioned previously, once released in the cell cytosol by the photochemical internalisation process, the antigenic molecule may be processed by the antigen-processing machinery of the cell and presented on the cell surface in an appropriate manner e.g. by Class I MHC. This processing may involve degradation of the antigen, e.g. degradation of a protein or polypeptide antigen into peptides, which peptides are then complexed with molecules of the MHC for presentation. Thus, the antigenic molecule expressed or presented on the surface of the cell according to the present invention may be a part or fragment of the antigenic molecule which is internalised (endocytosed).

A variety of different cell types can present antigen on their surface, including for example, lymphocytes (both T and B cells), dendritic cells, macrophages etc. Others include for example cancer cells e.g. melanoma cells. These cells are referred to herein as "antigen-presenting cells". "Professional antigen-presenting cells" which are cells of the immune system principally involved in the presentation of antigen to effector cells of the immune system are known in the art and described in the literature and include B lymphocytes, dendritic cells and macrophages. Preferably the cell is a professional antigen-presenting cell.

For antigen presentation by an antigen-presenting cell to a cytotoxic T-cell (CTL) the antigenic molecule needs to enter the cytosol of the antigen-presenting cell (Germain, Cell, 1994, 76, 287-299).

In embodiments of the invention, for example involving an in vitro or ex vivo method, or alternatively an in vivo method, the cell is a dendritic cell. Dendritic cells are immune cells forming part of the mammalian immune system. Their main function is to process antigenic material and present it on the surface to other cells of the immune system. Once activated, they migrate to the lymph nodes where they interact with T cells and B cells to initiate the adaptive immune response.

Dendritic cells are derived from hematopoietic bone marrow progenitor cells. These progenitor cells initially transform into immature dendritic cells which are characterized by high endocytic activity and low T-cell activation potential. Once they have come into contact with a presentable antigen, they become activated into mature dendritic cells and begin to migrate to the lymph node. Immature dendritic cells phagocytose pathogens and degrade their proteins into small pieces and upon maturation present those fragments at their cell surface using MHC molecules.

The dendritic cells may be derived from any appropriate source of dendritic cells, such as from the skin, inner lining of the nose, lungs, stomach and intestines or the blood. In a particularly preferred embodiment of the present invention the dendritic cells are derived from bone marrow.

Dendritic cells may be isolated from natural sources for use in the in vitro methods of the invention or may be generated in vitro. Dendritic cells arise from monocytes, i.e. white blood cells which circulate in the body and, depending on the right signal, can differentiate into either dendritic cells or macrophages. The monocytes in turn are formed from stem cells in the bone marrow. Monocyte-derived dendritic cells can be generated in vitro from peripheral blood mononuclear cells (PBMCs). Plating of PBMCs in a tissue culture flask permits adherence of monocytes. Treatment of these monocytes with interleukin 4 (IL-4) and granulocyte-macrophage colony stimulating factor (GM-CSF) leads to differentiation to immature dendritic cells (iDCs) in about a week. Subsequent treatment with tumor necrosis factor (TNF) further differentiates the iDCs into mature dendritic cells.

As used herein "contacting" refers to bringing the cells and the photosensitizing agent and/or the antigenic molecule and/or the cytokine as defined herein into physical contact with one another under conditions appropriate for internalization into the cells, e.g. preferably at 37° C. in an appropriate nutritional medium, e.g. from 25-39° C. or in vivo at body temperature, i.e. 36-38° C.

The cell may be contacted with the photosensitizing agent and antigenic molecule and the cytokine as defined herein sequentially or simultaneously. Preferably, and conveniently the components are contacted with the cell simultaneously. The photosensitizing agent and antigenic molecule (and optionally the cytokine) may be taken up by the cell into the same or different intracellular compartments (e.g. they may be co-translocated).

The cells are then exposed to light of suitable wavelengths to activate the photosensitizing compound which in turn leads to the disruption of the intracellular compartment membranes.

WO 02/44396 (which is incorporated herein by reference) describes a method in which the order of the steps in the method may be arranged such that for example the photosensitizing agent is contacted with the cells and activated by irradiation before the molecule to be internalised (in this case the antigenic molecule) is brought into contact with the cells. This method takes advantage of the fact that it is not necessary for the molecule to be internalised to be present in the same cellular subcompartment as the photosensitizing agent at the time of irradiation.

Thus in one embodiment, said photosensitizing agent and/or said antigenic molecule and/or the cytokine as defined herein are applied to the cell together, or separately relative to one another. Irradiation is then performed at a time when at least the antigenic molecule and photosensitizing agent appear in the same intracellular compartment. This is referred to as a "light after" method.

In an alternative embodiment, said method can be performed by contacting said cell with the photosensitizing agent first, followed by contact with the antigenic molecule and/or the cytokine as defined herein, and irradiation is performed after uptake of the photosensitizing agent into an intracellular compartment, but prior to the cellular uptake of the antigenic molecule (and optionally the cytokine) into an intracellular compartment containing said photosensitizing agent (e.g. it may be present in a different intracellular compartment at the time of light exposure), preferably prior to cellular uptake into any intracellular compartment, e.g. prior to any cellular uptake. Thus for example the photosensitizing agent may be administered followed by irradiation and then administration of the remaining agents. This is the so-called "light before" method.

"Internalisation" as used herein, refers to the intracellular, e.g. cytosolic, delivery of molecules. In the present case "internalisation" may include the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis or other appropriate uptake mechanisms, for example into or associated with intracellular membrane-restricted compartments, for example the endoplasmic reticulum, Golgi body, lysosomes, endosomes etc.

The step of contacting the cells with the various agents may be carried out in any convenient or desired way. Thus, if the contacting step is to be carried out in vitro the cells may conveniently be maintained in an aqueous medium, such as for example appropriate cell culture medium, and at the appropriate time point the various agents can simply be added to the medium under appropriate conditions, for example at an appropriate concentration and for an appropriate length of time. For example, the cells may be contacted with the agents in the presence of serum-free medium, or with serum-containing medium.

The comments below discuss the application of the various agents to the cells separately. As discussed above however, these agents may be applied to cells together, separately, simultaneously or sequentially. As referred to herein, the application of the various agents used in the methods of the invention may be to cells in vitro or in vivo. In the latter case, the application may be via direct (i.e.

localized) or indirect (i.e. systemic or non-localized) administration as described in more detail hereinbelow.

The photosensitizing agent is brought into contact with the cells at an appropriate concentration and for an appropriate length of time which can easily be determined by a skilled person using routine techniques, and will depend on such factors as the particular photosensitizing agent used and the target cell type and location. The concentration of the photosensitizing agent is conveniently such that once taken up into the cell, e.g. into, or associated with, one or more of its intracellular compartments and activated by irradiation, one or more cell structures are disrupted e.g. one or more intracellular compartments are lysed or disrupted. For example photosensitizing agents as described herein may be used at a concentration of for example 10 to 50 μg/ml. For in vitro use the range can be much broader, e.g. 0.0005-500 μg/ml. For in vivo human treatments the photosensitizing agent may be used in the range 0.05-20 mg/kg body weight when administered systemically. Alternatively, a range of 0.005-20 mg/kg body weight may be used for systemic administration. If administered locally, for example by intradermal, subcutaneous or intratumoural administration, the dose may be in the region of 1-5000 μg, for example 10-2500, 25-1000, 50-500, 10-300 or 100-300 μg. Preferably the dose is selected from 100 μg, 150 μg, 200 μg and 250 μg. Preferably the dose is 75-125 μg, e.g. 100 μg. The doses provided are for a human of average weight (i.e. 70 kg). For intradermal injection the photosensitiser dose may be dissolved in 100 μl-1 ml, i.e. the concentration may be in the range of 1-50000 μg/ml. In smaller animals the concentration range may be different and can be adjusted accordingly though when administered locally, little variation in dosing is necessary for different animals.

The concentration of antigen to be used will depend on the antigen which is to be used. Conveniently a concentration of 0.001-500 μg/ml (e.g. 20-500, 20-300, 20-100 μg/ml, 20-50, 10-50, 5-50, 1-50, 0.01-50, or 0.001-50 μg/ml) antigen may be used in vitro. For a peptide antigen a lower concentration e.g. of 0.001-500, e.g. 0.001-1, 5, 25, 50 or 100 μg/ml may be used. For a protein antigen a higher concentration of e.g. 0.5-500 μg/ml may be used. For in vivo use the protein antigen dose may be in the range 0.5-500 μg, for example 10-100 μg or 10-200 μg. For peptide antigens an in vivo dose of 0.1-4000 μg, e.g. 0.1-2000 μg, 0.1-1000 μg or 0.1-500 μg, for example 0.1-100 μg, may be employed. Such doses are appropriate for local administration. An appropriate concentration can be determined depending on the efficiency of uptake of the agent in question into the cells in question and the final concentration it is desired to achieve in the cells.

The concentration of the cytokine as defined herein will also depend on the particular molecule which is to be used. Conveniently, in vitro, a concentration as shown in the table below may be used. An in vivo dose, e.g. for local administration, of 5-500 μg, e.g. 50-250 μg, may be used for GM-CSF and 500,000-50,000,000 IU may be used for IFN-α. An in vivo concentration of 500,000-10,000,000 IU/kg (or IU/m²) may be used for IL-2; 1-500 μg/kg, e.g. 20-50 μg/kg may be used for IL-7, and 1-100 μg/kg, e.g. 10-50 μg/kg may be used for IL-15 and IL-21.

Table showing appropriate cytokine doses

|  | In vitro | Local (in vivo) |
| --- | --- | --- |
| GM-CSF | 0.05-5 ng/ml | 5-500 μg |
| IL-2 | 10-1000 IU/ml | 500,000-10,000,000 IU total dose or per m² |
| IL-7 | 0.5-100 ng/ml | 1-500 μg |
| IL-15 | 0.5-100 ng/ml | 1-100 μg |
| IL-21 | 0.5-500 ng/ml | 1-100 μg |
| IFN-alpha | 0.005-10 Units /ml | 500,000-10,000,000 IUnits |

In most cases the photosensitizing agent, the antigenic molecule and the cytokine as defined herein are administered together, but this may be varied. Thus different times or modes or sites of administration (or contact with the cell) are contemplated for each of the different components and such methods are encompassed within the scope of the invention.

In one embodiment the cytokine as defined herein is administered separately from the antigen, for example in a separate formulation, or systemically, e.g. via oral administration. Thus, in one embodiment the cytokine may be administered prior to administration of the antigen and/or photosensitiser, for example 24 hours before.

The cytokine may be administered separately relative to the other agents, e.g. approximately 2 hours prior to illumination. In an alternative embodiment the agent may be administered with or at the same time, i.e. simultaneously, as the antigen.

The contact between the cell and the photosensitizing agent and/or antigenic molecule and/or the cytokine as defined herein is conveniently from 15 minutes to 24 hours, e.g. 30 minutes to four hours, preferably from 1.5 to 2.5 hours. Alternatively, the range of time may be from about 1 hour to about 48 hours, for example from about 2 hours to about 40 hours, or from about 6 hours to about 36 hours, e.g. from 12 hours to 30 hours, e.g. 16 hours to 20 hours, for example 18 hours or about 18 hours.

In a preferred embodiment the initial incubation of the cell is with the photosensitising agent. In one embodiment the time between the administration of the photosensitizing agent and the antigenic molecule and/or cytokine is a matter of hours. For example, the photosensitizing agent may be applied 16 to 20 hours, e.g. 18 hours, before illumination, and the antigenic molecule and/or cytokine may be applied 1 to 3 hours, e.g. 2 hours before illumination. Thus, the time between the administration of the photosensitizing agent and the antigenic molecule and/or cytokine may be in the range of 15 to 23 hours.

Thus, the cell is then incubated with the antigen and/or cytokine as defined herein after the incubation with the photosensitiser. Conveniently the cells may be placed into photosensitizer/antigen-free medium after the contact with the photosensitizer/antigen and before irradiation, e.g. for 30 minutes to 4 hours, e.g. from 1.5 to 2.5 hours, depending on the timing of the incubation with the photosensitiser and antigenic molecule and cytokine.

In vivo an appropriate method and time of incubation by which the various agents are brought into contact with the target cells will be dependent on factors such as the mode of administration and the type of agents which are used. For example, if the agents are injected into a tumour, tissue or organ which is to be treated/irradiated, the cells near the injection point will come into contact with and hence tend to take up the agents more rapidly than the cells located at a greater distance from the injection point, which are likely to come into contact with the agents at a later time point and lower concentration. Conveniently a time of 6-24 hours may be used.

In addition, agents administered by intravenous injection or orally may take some time to arrive at the target cells and it may thus take longer post-administration e.g. several days, in order for a sufficient or optimal amount of the agents to accumulate in a target cell or tissue. The time of administration required for individual cells in vivo is thus likely to vary depending on these and other parameters.

Nevertheless, although the situation in vivo is more complicated than in vitro, the underlying concept of the present invention is still the same, i.e. the time at which the molecules come into contact with the target cells must be such that before irradiation occurs an appropriate amount of the photosensitizing agent has been taken up by the target cells and either: (i) before or during irradiation the antigenic molecule (and optionally the cytokine) has either been taken up, or will be taken up after sufficient contact with the target cells, into the cell, for example into the same or different intracellular compartments relative to the photosensitizing agent or (ii) after irradiation the antigenic molecule (and optionally the cytokine) is in contact with the cells for a period of time sufficient to allow its uptake into the cells.

For administration of agents described herein in vivo, any mode of administration common or standard in the art may be used, e.g. injection, infusion, topical administration, transdermal administration, both to internal and external body surfaces etc. For in vivo use, the invention can be used in relation to any tissue which contains cells to which the photosensitising agent containing compound or the molecule to be internalized is localized, including body fluid locations, as well as solid tissues. All tissues can be treated as long as the photosensitiser is taken up by the target cells, and the light can be properly delivered. Preferred modes of administration are intradermal, subcutaneous, topical or intratumoural administration or injection. Preferably administration is by intradermal injection.

To achieve the desired outcome, e.g. antigen presentation, generation of an immune response or vaccination, the methods or parts thereof may be repeated e.g. "re-vaccination" may take place. Thus, the method in its entirety may be performed multiple times (e.g. 2, 3 or more times) after an appropriate interval or parts of the method may be repeated, e.g. further administration of the cytokine as defined herein or additional irradiation steps. For example, the method or part of the method may be performed again a matter of days, e.g. between 5 and 60 days (for example 7, 14, 15, 21, 22, 42 or 51 days), e.g. 7 to 20 days, preferably 14 days, or weeks, e.g. between 1 and 5 weeks (for example, 1, 2, 3 or 4 weeks) after it was first performed. All or part of the method may be repeated multiple times at appropriate intervals of time, e.g. every two weeks or 14 days. In a preferred embodiment the method is repeated at least once. In another embodiment the method is repeated twice.

In one embodiment, in the second or subsequent time the method is carried out the antigenic molecule is administered in combination with the photosensitiser and illumination, i.e. the cytokine is not administered in the second or subsequent time the method is carried out.

In the embodiment wherein an adjuvant is used in the method (e.g. Poly(I:C)), in the second or subsequent time the method is carried out the antigenic molecule may be administered in combination with the photosensitiser and illumination, i.e. the adjuvant is not administered in the second or subsequent time the method is carried out. In this case the cytokine may be present or not in the second or subsequent time the method is carried out.

In an alternative embodiment, parts of the method of the invention may be carried out prior to the method of the invention being carried out. For example, the method may be carried out one or more times, for example twice, in the absence of cytokine before the method of the invention is carried out. Alternatively, the method may be carried out one or more times, for example twice, in the absence of photosensitiser and illumination before the method of the invention is carried out. Part of the method may be carried out a matter of days, e.g. 7 or 14 days, or weeks, e.g. 1, 3 or 4 weeks before the method of the invention is carried out. Part of the method may be repeated one or more times at these time intervals before the method of the invention is carried out. Thus, in a preferred aspect, the antigenic molecule is administered (e.g. to the subject) equal to or greater than 2 times (e.g. at the time intervals discussed above), wherein at least the administration of said antigenic molecule is performed in accordance with the method of the invention.

"Irradiation" to activate the photosensitising agent refers to the administration of light directly or indirectly as described hereinafter. Thus subjects or cells may be illuminated with a light source for example directly (e.g. on single cells in vitro) or indirectly, e.g. in vivo when the cells are below the surface of the skin or are in the form of a layer of cells not all of which are directly illuminated, i.e. without the screen of other cells. Illumination of the cell or subject may occur approximately 18-24 hours after administration of the photosensitizing agent, antigenic molecule and the cytokine as defined herein.

The light irradiation step to activate the photosensitising agent may take place according to techniques and procedures well known in the art. The wavelength of light to be used is selected according to the photosensitising agent to be used. Suitable artificial light sources are well known in the art, e.g. using blue (400-475 nm) or red (620-750 nm) wavelength light. For $TPCS_{2a}$ for example a wavelength of between 400 and 500 nm, more preferably between 400 and 450 nm, e.g. from 430-440 nm, and even more preferably approximately 435 nm, or 435 nm may be used. Where appropriate the photosensitiser, e.g. a porphyrin or chlorin, may be activated by green light, for example the KillerRed (Evrogen, Moscow, Russia) photosensitizer may be activated by green light.

Suitable light sources are well known in the art, for example the LumiSource® lamp of PCI Biotech AS. Alternatively, an LED-based illumination device which has an adjustable output power of up to 60 mW and an emission spectra of 430-435 nm may be used. For red light, a suitable source of illumination is the PCI Biotech AS 652 nm laser system SN576003 diode laser, although any suitable red light source may be used.

The time for which the cells are exposed to light in the methods of the present invention may vary. The efficiency of the internalisation of a molecule into the cytosol increases with increased exposure to light to a maximum beyond which cell damage and hence cell death increases.

A preferred length of time for the irradiation step depends on factors such as the target, the photosensitizer, the amount of the photosensitizer accumulated in the target cells or tissue and the overlap between the absorption spectrum of the photosensitizer and the emission spectrum of the light source. Generally, the length of time for the irradiation step is in the order of seconds to minutes or up to several hours (even up to 12 hours), e.g. preferably up to 60 minutes e.g. from 0.25 or 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Shorter irradiation times may also be used, for example 1 to 60 seconds, e.g. 10-50, 20-40 or 25-35 seconds.

Appropriate light doses can be selected by a person skilled in the art and again will depend on the photosensitizer used and the amount of photosensitizer accumulated in the target cells or tissues. The light doses are usually lower when photosensitizers with higher extinction coefficients (e.g. in the red area, or blue area if blue light is used, depending on the photosensitiser used) of the visible spectrum are used. For example, a light dose in the range of 0.24-7.2 J/cm$^2$ at a fluence range of 0.05-20 mW/cm$^2$, e.g. 2.0 mW/cm$^2$, may be used when an LED-based illumination device which has an adjustable output power of up to 60 mW and an emission spectra of 430-435 nm is employed. Alternatively, e.g. if the LumiSource® lamp is employed a light dose in the range of 0.1-6 J/cm$^2$ at a fluence range of 0.1-20 (e.g. 13 as provided by Lumisource®) mW/cm$^2$ is appropriate. For red light, a light dose of 0.03-1 J/cm$^2$, e.g. 0.3 J/cm$^2$, at a fluence range of 0.5-5 mW/cm$^2$, e.g. 0.81 mW/cm$^2$, may be used.

Furthermore, if cell viability is to be maintained, the generation of excessive levels of toxic species is to be avoided and the relevant parameters may be adjusted accordingly.

The methods of the invention may inevitably give rise to some cell damage by virtue of the photochemical treatment i.e. by photodynamic therapy effects through the generation of toxic species on activation of the photosensitizing agent. Depending on the proposed use, this cell death may not be of consequence and may indeed be advantageous for some applications (e.g. cancer treatment). In most embodiments, however, cell death is avoided to allow the generation of an immune response from the presenting cell. The methods of the invention may be modified such that the fraction or proportion of the surviving cells is regulated by selecting the light dose in relation to the concentration of the photosensitizing agent. Again, such techniques are known in the art.

Preferably, substantially all of the cells, or a significant majority (e.g. at least 75%, more preferably at least 80, 85, 90 or 95% of the cells) are not killed. In vitro cell viability following PCI treatment can be measured by standard techniques known in the art such as the MTS test. In vivo cell death of one or more cell types may be assessed within a 1 cm radius of the point of administration (or at a certain depth of tissue), e.g. by microscopy. As cell death may not occur instantly, the % cell death refers to the percent of cells which remain viable within a few hours of irradiation (e.g. up to 4 hours after irradiation) but preferably refers to the % viable cells 4 or more hours after irradiation.

The method may be performed in vivo, in vitro or ex vivo. Preferably the method is used in vitro or ex vivo to generate cells for administration in vivo or the method is used in vivo. Thus in a preferred feature, the method may be used to generate an immune response in a subject.

Thus, in a further aspect the present invention provides a method of generating an immune response in a subject, comprising administering to said subject an antigenic molecule, a photosensitizing agent, and a cytokine as defined hereinbefore, and irradiating said subject with light of a wavelength effective to activate said photosensitizing agent, wherein an immune response is generated.

An "immune response" which may be generated may be humoral and cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them and encompasses stimulating CTLs which forms a preferred aspect of the invention. Preferably the immune response which is stimulated is cytotoxic CD8 T cells. The extent of an immune response may be assessed by markers of an immune response, e.g. secreted molecules such as IL-2 or IFNγ or the production of antigen specific T cells (e.g. assessed as described in the Examples).

The stimulation of cytotoxic cells or antibody-producing cells, requires antigens to be presented to the cell to be stimulated in a particular manner by the antigen-presenting cells, for example MHC Class I presentation (e.g. activation of CD8$^+$ cytotoxic T-cells requires MHC-I antigen presentation). Preferably the immune response is stimulated via MHC-I presentation.

Preferably the immune response is used to treat or prevent a disease, disorder or infection, e.g. cancer. In methods and uses described herein the cancer may be melanoma. In alternative embodiments, the cancer may be a cancer which is not melanoma.

Preferably the method is used for vaccination. As referred to herein, "vaccination" is the use of an antigen (or a molecule containing an antigen) to elicit an immune response which is prophylactic or therapeutic against the development (or further development) of a disease, disorder or infection, wherein that disease, disorder or infection is associated with abnormal expression or presence of that antigen. Preferably the disease is cancer (and the vaccination is therapeutic) or an immune response is to be generated to an infection (and the vaccination is prophylactic).

In a preferred embodiment of the present invention, the subject of the method, e.g. vaccination, is a non-mammalian animal (e.g. a fish) or a mammal, preferably a cat, dog, horse, donkey, sheep, pig, goat, cow, mouse, rat, rabbit or guinea pig, but most preferably the subject is a human.

Preferably the methods described herein achieve synergy, i.e. the extent of cell surface presentation or the immune response generated is enhanced more than the combined enhancement observed by (i) performing the method with the antigenic molecule in the absence of the cytokine and (ii) performing the method with the antigenic molecule in the absence of the photosensitizing agent and the irradiation step, i.e. synergy between the methods is observed. The level of cell surface presentation or immune response generation may be assessed by appropriate means, e.g. number of antigen-specific CD8+ cells or levels of markers of immune response activation, e.g. IFNγ or IL-2.

"Synergy" as used to herein refers to a quantitative improvement over merely additive effects.

The various agents used in the methods of the invention may be administered to the subject separately, sequentially or simultaneously.

Aspects and features discussed above in relation to the method of expressing an antigenic molecule or a part thereof on the surface of a cell of the present invention, where appropriate, are also applicable to the method of generating an immune response above.

The invention also provides a method for introducing an antigenic molecule into the cytosol of a cell, comprising contacting said cell with the antigenic molecule to be introduced, a photosensitising agent and a cytokine as defined herein, and irradiating the cell with light of a wavelength effective to activate the photosensitising agent. Once activated, intracellular compartments within said cell containing said compound release the molecule contained in these compartments into the cytosol.

The methods of the invention above may be used in vitro or in vivo, for example either for in situ treatment or for ex vivo treatment followed by the administration of the treated cells to the body.

The invention further provides a cell expressing an antigenic molecule, or a part thereof, on its surface, or a population thereof, which cell is obtainable (or obtained) by any of the methods as defined herein. Also provided is the cell or cell population for use in prophylaxis, or therapy, as described hereinafter.

The cell population may be provided in a pharmaceutical composition comprising in addition one or more pharmaceutically acceptable diluents, carriers or excipients.

The present invention also provides a pharmaceutical composition comprising an antigenic molecule, a photosensitizing agent, and a cytokine as defined herein and one or more pharmaceutically acceptable diluents, carriers or excipients.

These compositions (and products of the invention) may be formulated in any convenient manner according to techniques and procedures known in the pharmaceutical art, e.g. using one or more pharmaceutically acceptable diluents, carriers or excipients. "Pharmaceutically acceptable" as referred to herein refers to ingredients that are compatible with other ingredients of the compositions (or products) as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule (or components of the composition or product), purpose of treatment, age of patient, mode of administration etc. In connection with the photosensitizing agent, the potency/ability to disrupt membranes on irradiation, should also be taken into account.

The cells, for example antigen presenting cells, may be prepared in vitro. In treatment methods, these cells may be administered to a body in vivo or a body tissue ex vivo such that those cells may stimulate an immune response, e.g. for prophylactic or therapeutic purposes.

Thus the invention further provides a cell population (or composition containing the same) as defined herein, or an antigenic molecule, a photosensitizing agent, and a cytokine as defined herein, for use in prophylaxis or therapy or for use in stimulating an immune response, for example for vaccination purposes, e.g. for stimulating CTLs, in a subject, preferably for treating or preventing a disease, disorder or infection in said subject, particularly for treating or preventing cancer. Alternatively defined the present invention provides use of (i) a cell population, (ii) a composition as defined herein, or (iii) an antigenic molecule and/or a photosensitizing agent and/or a cytokine, for the preparation of a medicament for use in stimulating an immune response (e.g. for stimulating CTLs) in a subject, preferably for treating or preventing a disease, disorder or infection in said subject, preferably for vaccination and/or for treating or preventing cancer, wherein preferably said immune response is stimulated by a method as defined herein.

Said stimulation, treatment or prevention preferably comprises administering said medicament to said subject.

The antigenic molecule, photosensitizing agent and the cytokine may be combined and presented in a composition. Alternatively expressed, the invention provides use of an antigenic molecule and/or a photosensitizing agent and/or a cytokine as defined herein in the manufacture of a medicament for stimulating an immune response (e.g. for stimulating CTLs in a subject), preferably to treat or prevent a disease, disorder or infection in said subject, particularly for vaccination purposes, wherein said medicament comprises a population of cells expressing an antigenic molecule or a part thereof on the surface of said cells obtainable by a method as defined herein, for administration to said subject. Preferably the cell population is obtained by such methods. The population is for administration to the subject.

In an alternative embodiment the present invention provides an antigenic molecule, photosensitizing agent and cytokine as defined herein for use in expressing said antigenic molecule or a part thereof on the surface of a cell to stimulate an immune response (e.g. for stimulating CTLs) in a subject, preferably to treat or prevent a disease, disorder or infection in said subject, wherein said use comprises a method as defined herein, preferably to prepare a population of cells, e.g. dendritic cells. These cells may then be administered to the subject.

The invention further provides a product comprising an antigenic molecule, photosensitizing agent and cytokine as defined herein as a combined preparation for simultaneous, separate or sequential use in stimulating an immune response in a subject (or for expressing an antigenic molecule or a part thereof on the surface of a cell or for internalising an antigenic molecule into the cytosol of a cell) in a method as defined herein, preferably to treat or prevent a disease, disorder or infection in a subject.

The present invention also provides a kit for use in stimulating an immune response in a subject, preferably for treating or preventing a disease, disorder or infection in said subject, for example for use in vaccination or immunisation, or for expressing an antigenic molecule or a part thereof on the surface of a cell or for internalising an antigenic molecule into the cytosol of a cell in a method as defined herein, said kit comprising a first container containing a photosensitizing agent as defined herein;

a second container containing said antigenic molecule as defined herein;

and a third container containing a cytokine as defined herein.

The products and kits of the invention may be used to achieve cell surface presentation (or therapeutic methods) as defined herein.

In a yet further embodiment the present invention provides a method of generating an immune response (e.g. for stimulating CTLs) in a subject, preferably to treat or prevent a disease, disorder or infection in said subject, comprising preparing a population of cells according to the method defined herein, and subsequently administering said cells to said subject.

The antigenic presentation achieved by the claimed invention may advantageously result in the stimulation of an immune response when the treated cells are administered in vivo. Preferably an immune response which confers protection against subsequent challenge by an entity comprising or containing said antigenic molecule or part thereof is generated, and consequently the invention finds particular utility as a method of vaccination.

The disease, disorder or infection is any disease, disorder or infection which may be treated or prevented by the generation of an immune response, e.g. by eliminating abnormal or foreign cells which may be identified on the basis of an antigen (or its level of expression) which allows discrimination (and elimination) relative to normal cells.

Selection of the antigenic molecule to be used determines the disease, disorder or infection to be treated. Based on the antigenic molecules discussed above, the methods, uses, compositions, products, kits and so forth, described herein may be used to treat or prevent against, for example, infections (e.g. viral or bacterial as mentioned hereinbefore), cancers or multiple sclerosis. Prevention of such diseases, disorders or infection may constitute vaccination.

As defined herein "treatment" refers to reducing, alleviating or eliminating one or more symptoms of the disease, disorder or infection which is being treated, relative to the symptoms prior to treatment. "Prevention" (or prophylaxis) refers to delaying or preventing the onset of the symptoms of the disease, disorder or infection. Prevention may be absolute (such that no disease occurs) or may be effective only in some individuals or for a limited amount of time.

For in vivo administration of the cells, any mode of administration of the cell population which is common or standard in the art may be used, e.g. injection or infusion, by an appropriate route. Conveniently, the cells are administered by intralymphatic injection. Preferably $1 \times 10^4$ to $1 \times 10^8$ cells are administered per kg of subject (e.g. $1.4 \times 10^4$ to $2.8 \times 10^6$ per kg in human). Thus, for example, in a human, a dose of $0.1$-$20 \times 10^7$ cells may be administered in a dose, i.e. per dose, for example as a vaccination dose. The dose can be repeated at later times if necessary.

The invention will now be described in more detail in the following non-limiting Examples with reference to the following drawings in which:

FIG. 1A shows Scheme 1: synthetic route for synthesis of compound 5. Reagents and conditions: (a) propionic acid, reflux, 1 h (20%); (b) NaNO$_2$ (1.8 eq), TFA, rt, 3 min. 67%); (c) SnCl$_2$.2H$_2$O, conc. HCl, 60° C., 1 h (88%); (d) Bromoacetyl bromide, Et$_3$N, CH$_2$Cl$_2$, rt, 1 h (64%) (e) Piperazine, CH$_2$Cl$_2$, rt, 1 h (94%).

Figure 1B:
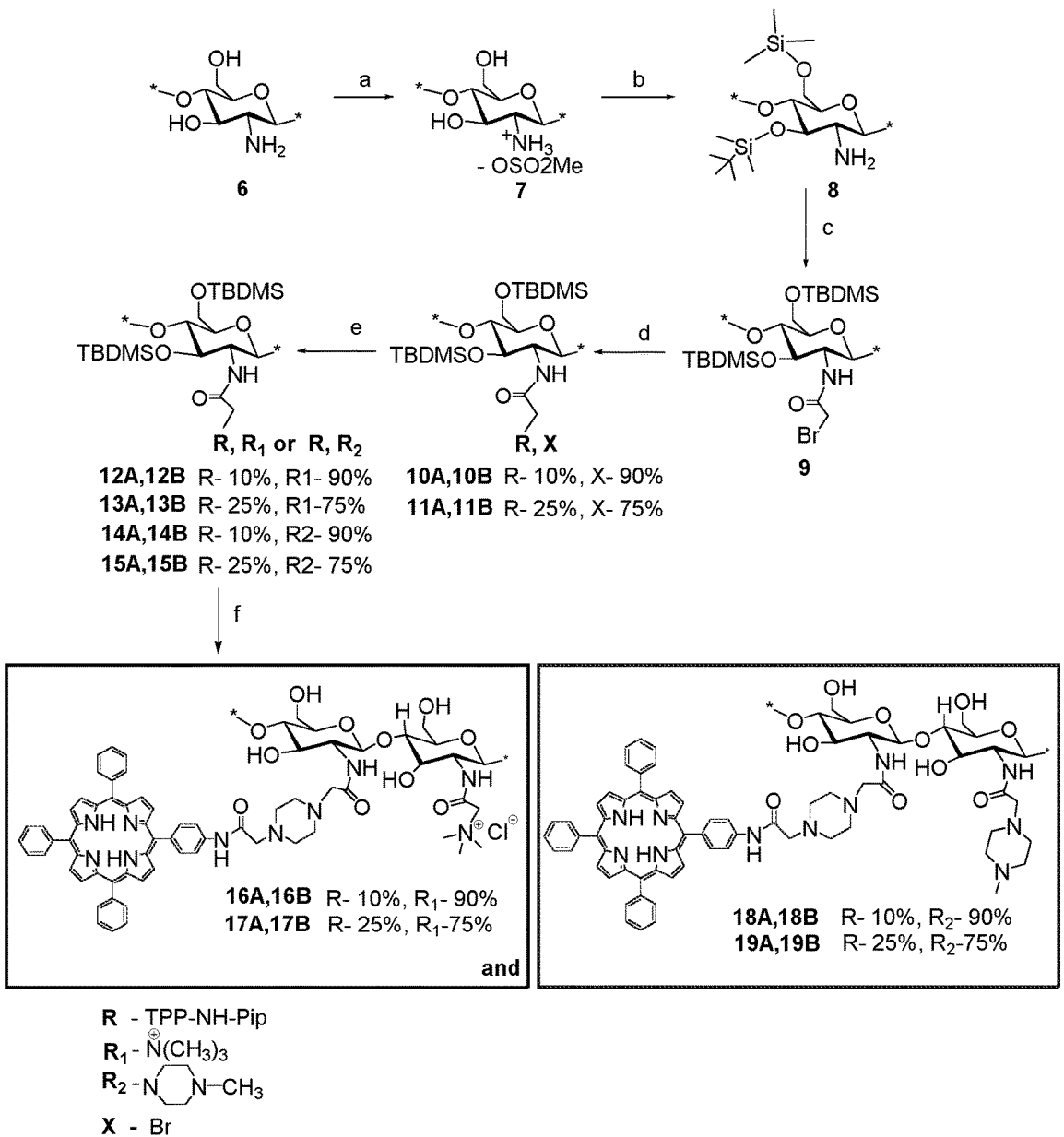

FIG. 1B shows Scheme 2. Synthesis of N-modified Chitosan derivatives (TPP-CS-TMA & TPP-CS-MP). Here A-represents 1$^{st}$ batch compounds and B-presents 2$^{nd}$ batch compounds. Reagents and conditions: (a) MeSO$_3$H/H$_2$O, 10° C.-rt, 1 h, (90%); (b) TBDMSCl, imidazole, DMSO, rt, 24 h (96%); (c) Bromoacetyl bromide, Et$_3$N, CH$_2$Cl$_2$, −20° C., 1 h (92%); (d) compound 5 i.e. TPP-NH-Pip (0.1 or 0.25 eq), Et$_3$N, CHCl$_3$, rt, 2 h (92-90%) (e) NMe$_3$ or 1-methyl piperazine, CHCl$_3$, rt, 24 h (f) TBAF, NMP, 55° C., 24 h or conc. HCl/MeOH, rt, 24 h.

Figure 1C:
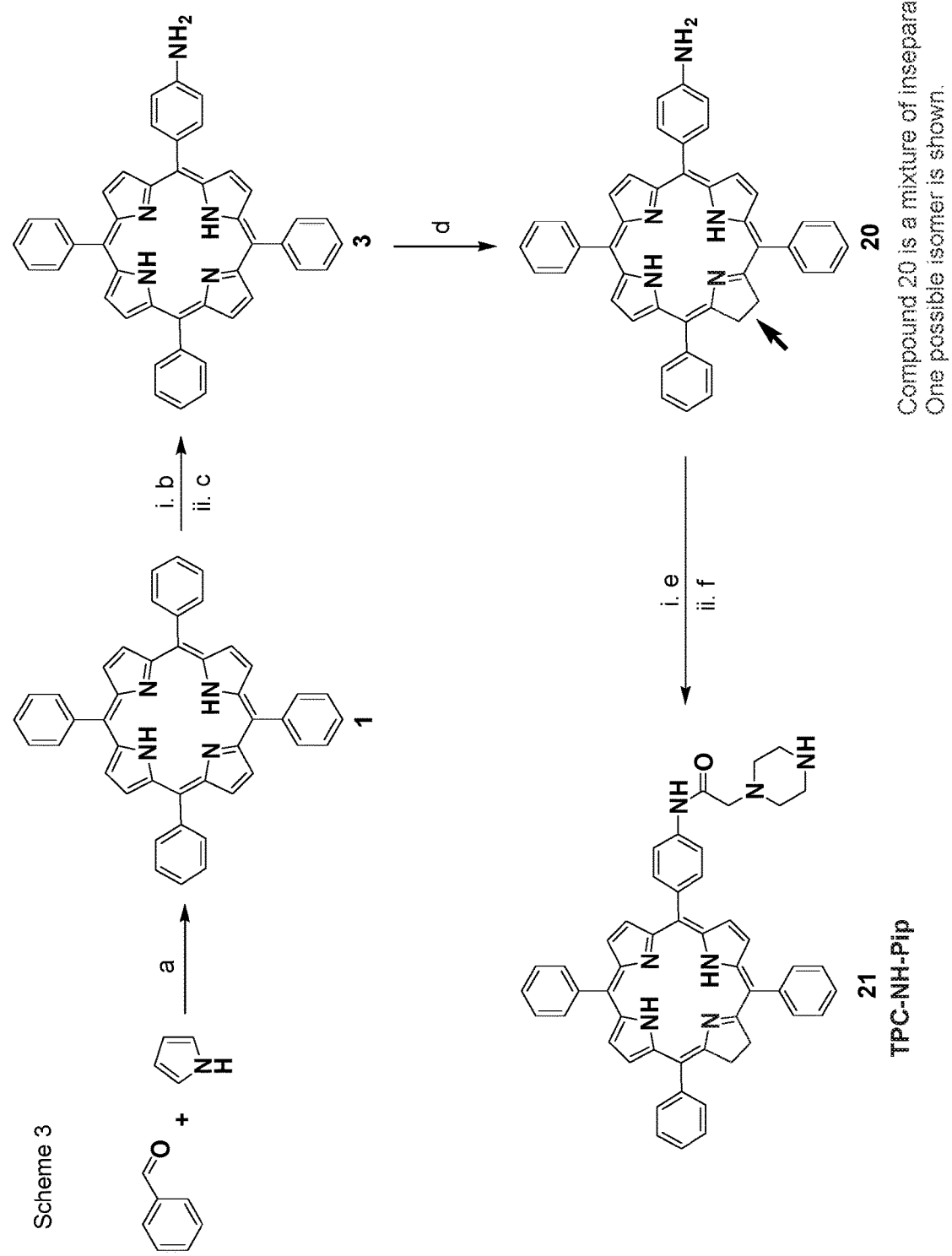

FIG. 1C shows Scheme 3—Synthesis scheme for compounds 1, 3 20 and 21. Reactions and conditions: ((a) Propionic acid, reflux, 1 h, (20%); (b) NaNO$_2$ (1.8 eq.), TFA, rt, 3 min.; (c) SnCl$_2$.2H$_2$O, conc. HCl, 60° C., 1 h, (54%); (d$_1$) p-Toluenesulfonylhydrazide, K$_2$CO$_3$, pyridine, reflux, 24 h; (d$_2$) o-Chloranil, CH$_2$Cl$_2$, rt, (80%); (e) Chloroacetyl chloride, Et$_3$N, CH$_2$Cl$_2$, rt, 2 h, in situ-(f) Piperazine, CH$_2$Cl$_2$, rt, 12 h, (61%). All derivatives of compound 20 and 21 will contain the TPCa$_1$ and the TPCa$_2$ isomer. However only the TPCa$_1$ structure is shown in schemes and in the structure drawings.

Figure 1D:
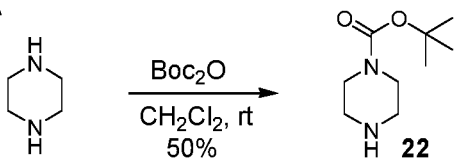
Figure 1D:
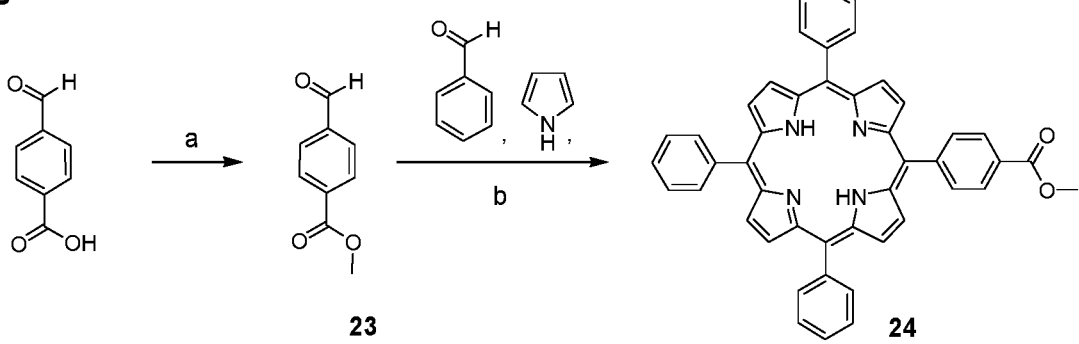
Figure 1D:
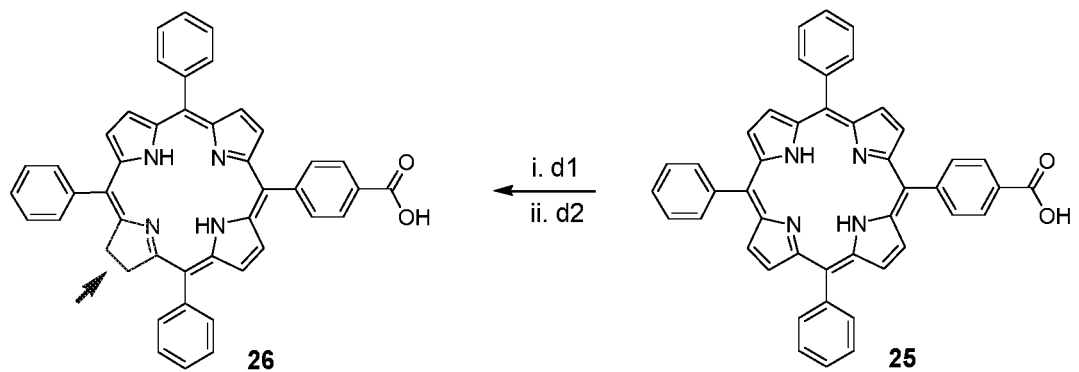
Figure 1D:
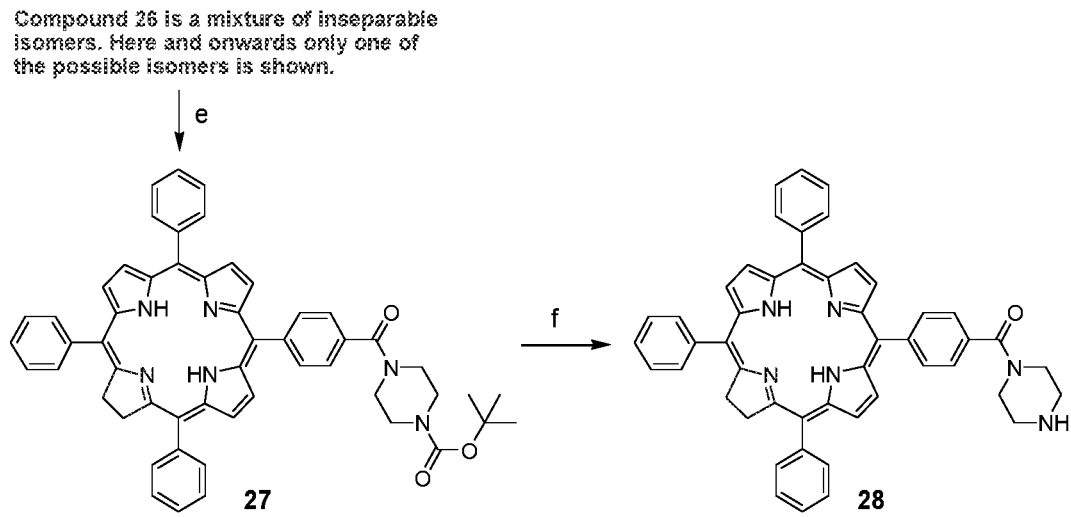

FIG. 1D shows Scheme 4-synthesis scheme for compounds 22-28. Reactions and conditions: (a) Acetyl chloride, MeOH, reflux, 24 h, (87%); (b) BF$_3$.Et$_2$O, CHCl$_3$, rt, p-chloranil, 48 h, (14%); (c) 2N KOH (in MeOH), THF: Pyridine (10:1), reflux, 24 h (71%); (d$_1$) p-Toluenesulfonyl-hydrazide, K$_2$CO$_3$, Pyridine, reflux, 24 h; (d$_2$) o-chloranil, CH$_2$Cl$_2$: MeOH (75:25), rt, (70%); (e) EDCI.HCl, HOBT, Et$_3$N, N-Boc-piperazine 5, DMF, rt, 24 h (54%) (f) TFA, CH$_2$Cl$_2$, rt, 1 h (89%). All derivatives of compound 26-28 will contain the TPCc$_1$ and the TPCc$_2$ isomer. However, only the TPCc$_1$ structure is shown in schemes and in the structure drawings.

Figure 1E:
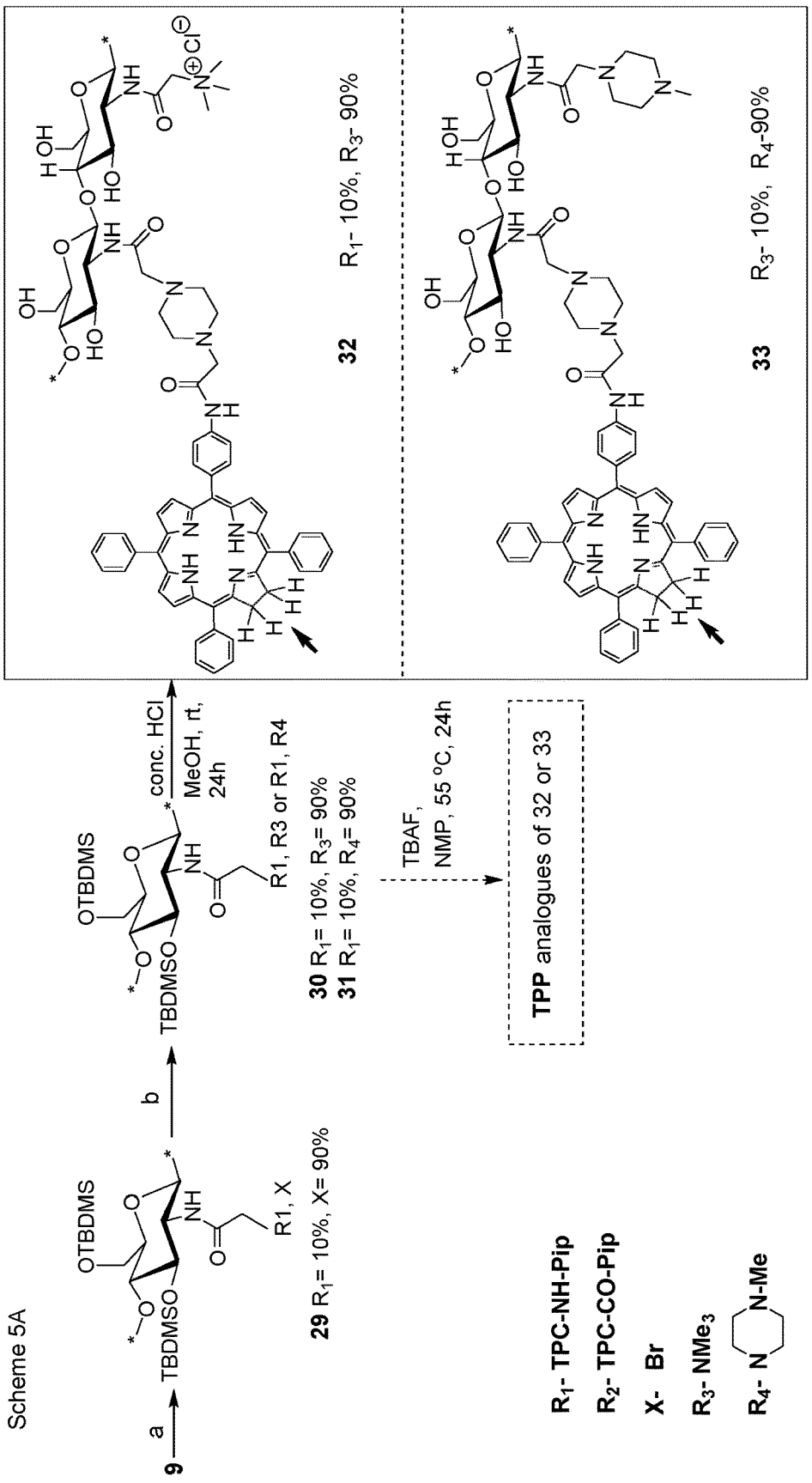
Figure 1F:
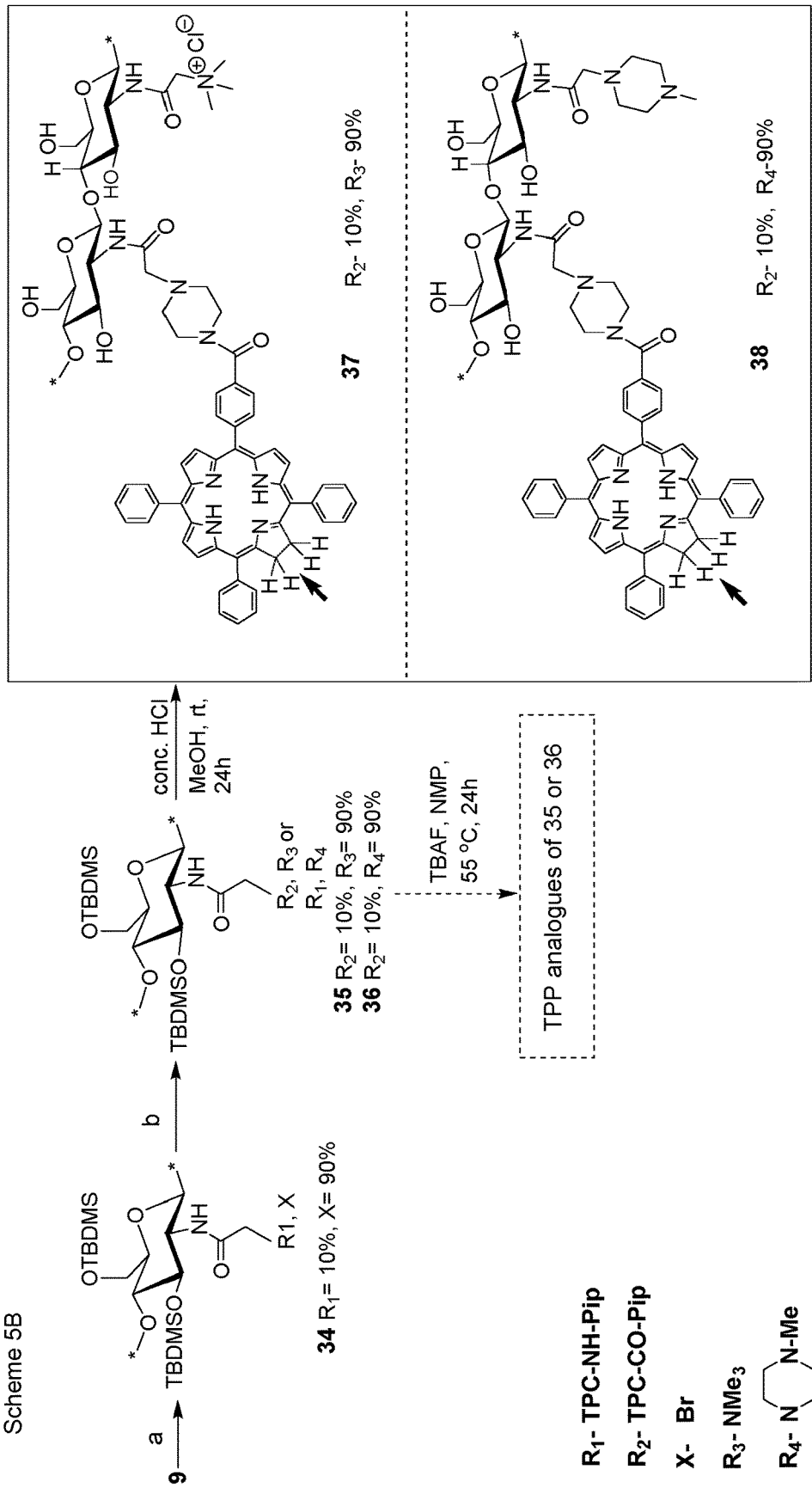

FIGS. 1E-1F show Scheme 5A and Scheme 5B, respectively. Reagents and conditions (6A): (a) compound 21 i.e. TPC-NH-Pip (0.1 eq), Et$_3$N, CHCl$_3$, rt, 2 h (78%) (b) NMe$_3$ or 1-methyl piperazine, CHCl$_3$, rt, 24 h. Reagents and conditions (6b): a) compound 28 i.e. TPC-CO-Pip (0.1 eq), Et$_3$N, NMP, 75° C., 12 h (89%) (b) NMe$_3$ or 1-methyl piperazine, CHCl$_3$, rt, 24 h.

Figure 2A:
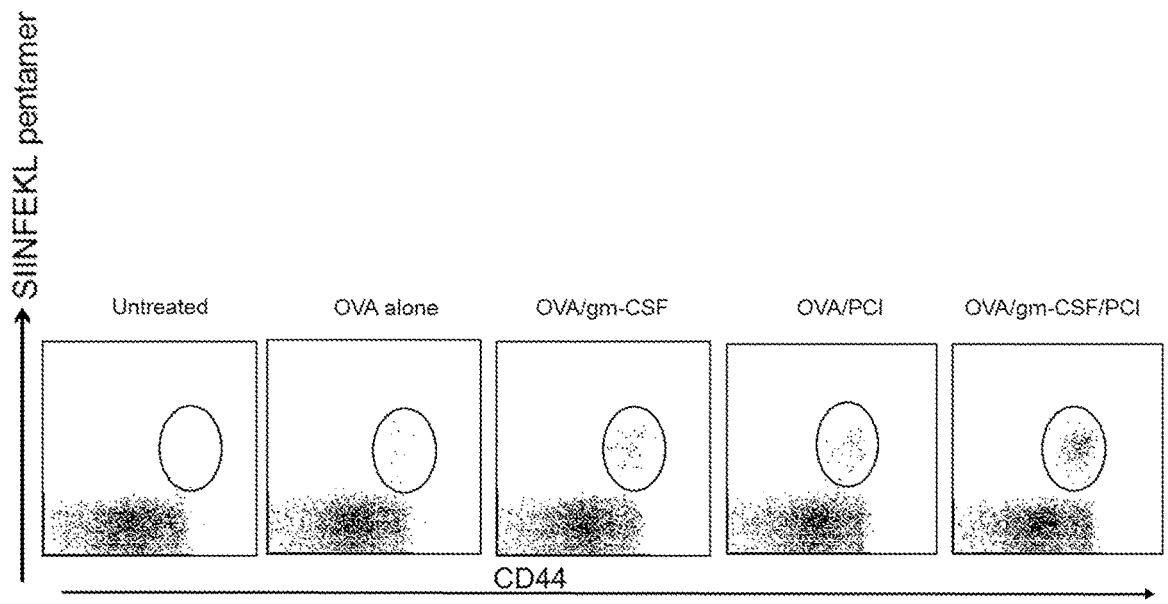
Figure 2B:
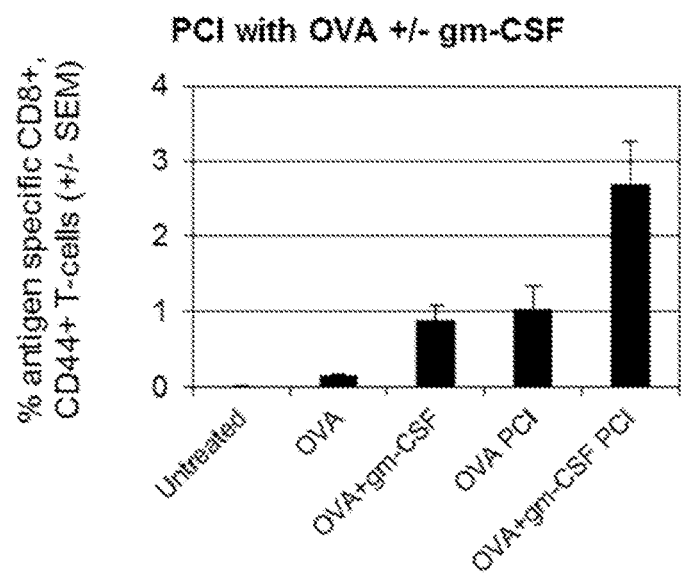

FIGS. 2A-2B show the effect of the adjuvant GM-CSF. Mice were immunised with 10 μg OVA, with 10 μg OVA and 10 μg GM-CSF, with 10 μg OVA and 150 μg TPCS$_{2a}$, with 10 μg OVA, 10 μg GM-CSF, and 150 μg TPCS$_{2a}$ or left untreated. Mice receiving TPCS$_{2a}$ were illuminated. On day 7 the mice were bled, and the frequency of OVA-specific CD8 T-cells was analyzed by flow cytometry. (FIG. 2A) shows representative dot plots from the flow cytometry analysis. The cells were first gated on CD8 expression, and then the CD8$^+$ population was analysed for SIINFEKL pentamer binding (y-axis) and CD44 expression (x-axis). The population within the ellipses thus represents the CD8$^+$, pentamer$^+$, CD44$^+$ cells, representing the antigen-specific (pentamer binding), activated (CD44 expression) CD8$^+$ cells. (FIG. 2B) shows the average values (% antigen-specific, CD44$^+$ cells of the total CD8+ cells) for the experimental groups (5 animals in each group, error bars: standard error of the mean).

Figure 3:
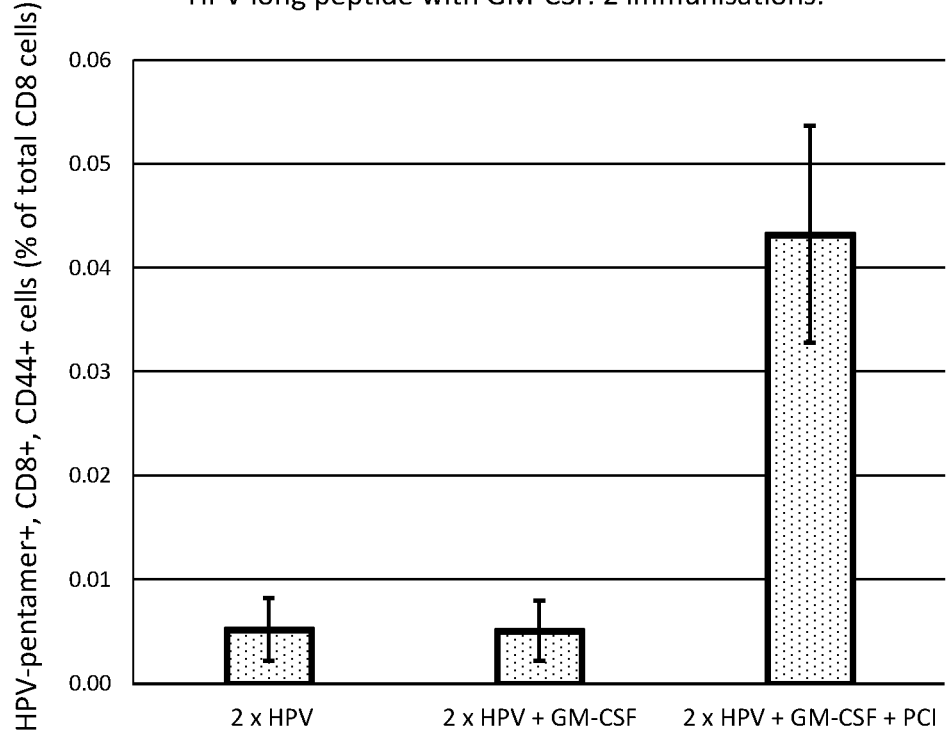

FIG. 3 shows the effect of GM-CSF on vaccination of mice with a HPV 16 E7 peptide antigen. Mice were immunised with HPV alone or HPV with GM-CSF, with or without PCI. The figure shows the % of total CD8 cells expressing the HPV pentamer.

Figure 4:
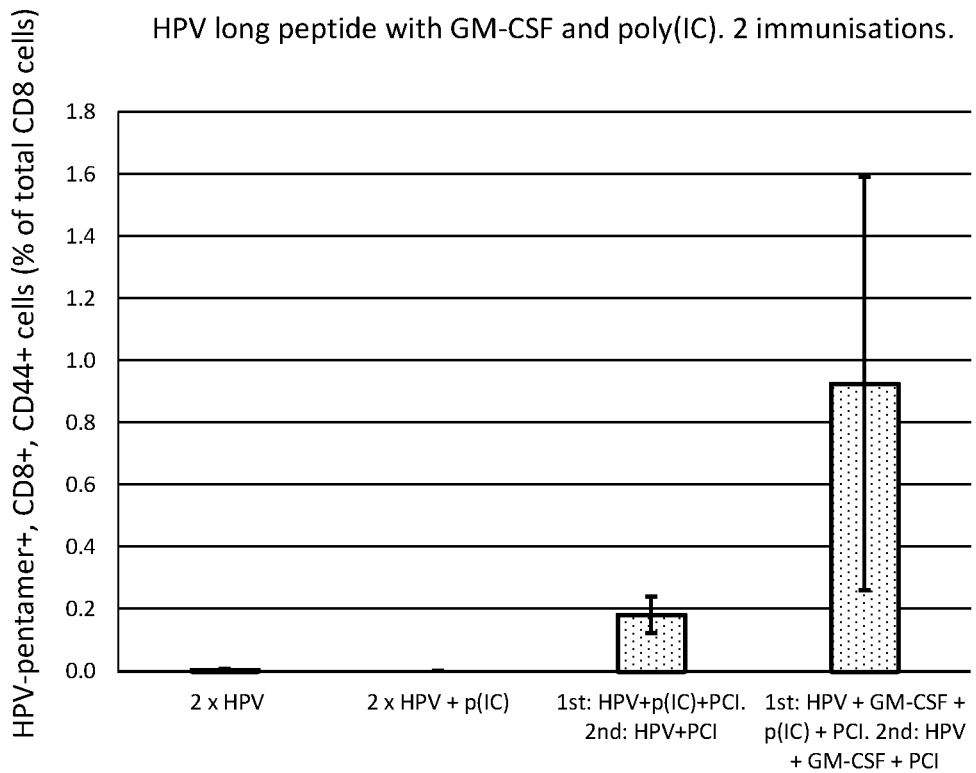

FIG. 4 shows the effect of GM-CSF, optionally with Poly(IC) on vaccination of mice with a HPV 16 E7 peptide antigen. Mice were immunised with HPV, poly(IC) and/or GM-CSF with or without PCI, as indicated in the figure. 2 immunisations were used in the results shown in the last two bars in the figure. The figure shows the % of total CD8 cells expressing the HPV pentamer.

EXAMPLES

Example 1

Effect of Cytokines on In Vivo Vaccination with OVA

Materials and Methods

Mice

C57BL/6 mice are purchased from Harlan (Horst, The Netherlands). OT-I mice transgenic for the T-cell receptor that recognises the MHC class-I restricted epitope OVA$_{257-264}$ from ovalbumin (OVA) are bred in facilities at the University of Zurich (originally purchased from Taconic Europe (Ry, Denmark)). All mice are kept under specified pathogen-free (SPF) conditions, and the procedures performed are approved by Swiss Veterinary authorities. In the OT-1 mice, the gene for the T-cell receptor has been engineered in such a way that nearly all of the CD8+ T-cells in these mice (called OT-1 cells) will specifically recognize the specific peptide epitope (SIINFEKL) from the ovalbumin (OVA) antigen.

Immunisation Protocol

On day 0 female C57BL/6 mice are injected with $1.5 \times 10^6$ splenocytes from Rag2/OT-1 mice intravenously in the tail vein. In this way the mice that are vaccinated have a "background" of CD8 T-cells that can respond to the SIINFEKL-epitope from OVA if, and only if, this is properly presented on MHC class I on antigen presenting cells. Thus, the transfer of OT-1 cells "amplifies" the detection system in the vaccinated mice making it possible to easily assay for the effect of in vivo vaccination by measuring antigen specific CD8+ T-cells and IFN-y and IL-2 production.

4 hours later the animals are vaccinated by intradermal injection at the abdomen (2×50 µl of solutions containing the ingredients specified below). 14 groups of 4 animals receive total doses of:
- Group 1: 250 µg $TPCS_{2a}$ (Amphinex)+10 µg ovalbumin (OVA, Grade V, Sigma-Aldrich).
- Group 2: 250 µg $TPCS_{2a}$+10 µg ovalbumin+10 µg GM-CSF.
- Group 3: 250 µg $TPCS_{2a}$+10 µg ovalbumin+500 000 IU IL-2.
- Group 4: 250 µg $TPCS_{2a}$+10 µg ovalbumin+10 µg IL-7.
- Group 5: 250 µg $TPCS_{2a}$+10 µg ovalbumin+10 µg IL-15.
- Group 6: 250 µg $TPCS_{2a}$+10 µg ovalbumin+10 µg IL-21.
- Group 7: 250 µg $TPCS_{2a}$+10 µg ovalbumin+3,000,000 IU IFNα.
- Group 8: 10 µg ovalbumin.
- Group 9: 10 µg ovalbumin+25 µg GM-CSF.
- Group 10: 10 µg ovalbumin+500,000 IU IL-2.
- Group 11: 10 µg ovalbumin+10 µg IL-7.
- Group 12: 10 µg ovalbumin+10 µg IL-15.
- Group 13: 10 µg ovalbumin+10 µg IL-21.
- Group 14: 10 µg ovalbumin+3,000,000 IU IFNα.

On day 1 the animals of groups 1-7 are anaesthetized and illuminated for 6 minutes with blue light using a LumiSource lamp (PCI Biotech AS). The animals are illuminated about 18 h after injection of the antigen solution, the fluence rate of the illumination is about 13 mW/cm². On day 7 the mice are bled from the tail vein and the blood cells are stained with SIINFEKL pentamer (ProImmune), and CD8 and CD44 antibodies for flow cytometry analysis (see protocols below). On day 14 the mice are euthanized and the spleens are collected. One aliquot of the splenocytes is restimulated with the SIINFEKL peptide (EMC microcollections, Tuebingen, Germany), stained for intracellular IFN-γ expression and analysed by Flow cytometry analysis (see below). Another aliquot of the splenocytes is resuspended in cell culture medium, kept in this medium overnight (purely for practical reasons) without restimulation stained by SIINFEKL-pentamer as described above and analysed by flow cytometry (see protocol below).

SIINFEKL-Pentamer-Staining of Spleen Cells

SIINFEKL-pentamer staining and flow cytometry on spleen cells is performed on cells that have been resuspended in cell medium and kept in this medium overnight (purely for practical reasons) without restimulation.

SIINFEKL-Pentamer Staining and Flow Cytometry 5-10 drops of whole tail blood are collected and 0.5 ml of Red Cell Lyse solution (Sigma) is added. After 5-6 minutes, cells are spun down and washed twice with 0.5 ml PBS. The cell pellet is resuspended in FACS buffer (2% FCS/PBS with 0.01% Na-azide), transferred to a U-formed 96 well plate and incubated with FcR-blocking antibodies (1.0 µl Anti-CD16/CD32 from Pharmingen) for 10 min on ice, (1 µl+49 µl FACS buffer). Without washing, the SIINFEKL-pentamer-PE (ProImmune; 5 µl per sample) is added, mixed and incubated at 37° C. for 15 min. Without washing, a fluorescence-labeled CD8 or CD44 is added to a final concentration of 1:100, and incubated on ice for 25-45 min. Cells are washed in 100 µl FACS buffer and suspended in 100 µl FACS buffer. Cells are analysed with FACSCanto.

Splenocyte Restimulation Ex Vivo

Splenocytes are isolated and prepared for intracellular staining by crushing the spleen and separating cells in 2% FCS/PBS, by agitation in lysis buffer (Sigma) for 1-2 minutes and washing in 2% FCS/PBS. 1 ml of the cell suspension in complete medium is added per well of a 24-well plate (500,000 cells/ml) and 5 µg/ml SIINFEKL is added to each well and incubated overnight at 37° C. Brefeldin A (1-2 µg/ml) is added to each well and incubated for 4 hours at 37° C. Cells are transferred to U-formed 96 well plates, washed in 2% FCS/PBS and resuspended in 50 µl FACS buffer with FcR-blocking antibodies (1.0 µl anti-CD16/CD32 from Pharmingen), and incubated on ice for 10 minutes. Without washing, cells are incubated with surface antibodies CD8 or CD44 for 20-45 min on ice (dark), washed in FACS buffer and fixed by resuspending in 100 µl paraformaldehyde (PFA) (1% in PBS) for 10-20 minutes on ice. Cells are washed in FACS buffer, resuspended in 100 µl NP40 (0.1% in PBS) and incubated for 3 minutes on ice. After washing in FACS buffer, a fluorescence-labelled interferon-gamma antibody is added and incubated for 35 min on ice in the dark. After washing and suspension in FACS buffer, the cells are analysed with FACSCanto using FlowJo 8.5.2 software (Tree Star, Inc., Ashland, Oreg.).

Flow Cytometry

The frequency of OVA-specific T-cells is determined by flow cytometry (FACSCanto from BD Biosciences, San Jose, USA). Before the flow cytometry run a compensation is performed using beads stained with each antibody separately. Before antibody staining, the red blood cells are lysed using Red Cell Lyse solution (Sigma). 10 000 $CD8^+$ events are recorded for each sample, and the percentage of SIINFEKL-pentamer positive cells is calculated using FlowJo 8.5.2 software from Tree Star, Inc. (Ashland, Oreg.) http://www.flowjo.com/.

ELISA

ELISA is performed using the Ready-set Go! kit (eBioscience) for the relevant molecules according to the manufacturer's instructions.

Mice are vaccinated in vivo by the immunisation protocol described above. Blood is isolated after 7 days and spleen after 14 days. Blood is analysed for antigen-specific CD8+ T cells and spleen cells are either analysed directly for antigen-specific CD8+ T-cells or for IFN-γ or IL-2 production after restimulation in vitro.

Level of Antigen-Specific T-cells in Blood and Spleen

The level of antigen-specific T-cells is measured by flow cytometry, using a fluorescently labelled antigen-specific "pentamer" that binds specifically to the antigen-specific T-cells. The number of antigen specific CD8+ T-cells in % of the total CD8+ T-cells in the animal is determined (see the staining and flow cytometry analysis described in the immunisation protocol and details of SIINFEKL staining).

The endogenous T-cells serve as an internal control for the antigen-specificity of the effect, since a general stimulation effect on T-cells will affect also the endogenous T-cells not leading to an increase in the % of the antigen-specific cells. Typically the % of OT-1 cells is measured before vaccination and at time point(s) after vaccination. The effect of the antigen alone ("conventional vaccination") is compared to the effect of antigen+PCI.

Level of IFN-γ Production in Spleen Cells after Ex Vivo Stimulation with Antigen (Flow Cytometry)

Spleens removed on day 14 of vaccination are subject to splenocyte isolation and restimulation with SIINFEKL antigen peptide and intracellular staining for IFN-γ production for analysis of CD8+ T cells by flow cytometry as described in the protocols above.

Level of IFN-γ and IL-2 Production in Spleen Cells after Ex Vivo Stimulation with Antigen (ELISA)

Spleens removed on day 14 of vaccination are subject to splenocyte isolation and restimulation with SIINFEKL antigen peptide and IFN-γ and IL-2 production analysis by ELISA as described in the protocols above.

Example 2

Effect of GM-CSF on In Vivo Vaccination with OVA

Materials and Methods
Animals

C57BL/6 mice were purchased from Harlan (Horst, The Netherlands). CD8 T-cell receptor transgenic OT-I mice (B6.129S6-Rag2tm1Fwa Tg(TcraTcrb)1100 Mjb) were purchased from Taconic Europe (Ry, Denmark) or from Jackson Laboratories (Bar Harbor, Me.). The OT-I CD8 T cells recognise the H-2K$^b$-restricted epitope SIINFEKL from ovalbumin (OVA, aa257-264). All mice were kept under SPF conditions, and the procedures performed were approved by the veterinary authorities in Switzerland and Norway.

Materials and Cells

Chicken OVA was purchased from Sigma-Aldrich (Buchs, Switzerland), the SIINFEKL peptide from EMC microcollections (Tuebingen, Germany), and GM-CSF from Preprotech (Wien). The photosensitiser tetraphenyl chlorine disulfonate (TPCS$_{2a}$) was from PCI Biotech (Lysaker, Norway). OVA, TPCS$_{2a}$ and, when relevant, GM-CSF were mixed in PBS, kept light protected, and administered to mice within 60 minutes of preparation. TPCS$_{2a}$ was activated by illumination with LumiSource™ (PCI Biotech).

Intradermal Photosensitisation and Immunisation of Mice

One day prior to the immunisation, spleens and lymph nodes were isolated from female OT-1 mice, and erythrocytes were removed by lysis (RBC Lysing Buffer Hybri-Max from Sigma-Aldrich) from the homogenised cell suspensions. The remaining cells were washed in PBS, filtered through 70 micron nylon strainers, and 2×10$^6$ OT-1 cells were administered by intravenous injection into recipient female C57BL/6 mice; the adoptive transfer of SIINFEKL-specific CD8 T cells facilitates monitoring of the immune response by flow cytometry. One day or 8 hours later, mice were bled by tail bleeding, and the blood was collected in heparin-containing tubes for analysis of the baseline frequency of OVA-specific CD8 T cells.

Then, the mice were shaved on the abdominal area, and the vaccines, consisting of OVA or of different mixtures of OVA, TPCS$_{2a}$ and GM-CSF (10 µg) were injected intradermally using syringes with 29 G needles. The vaccines were kept light protected and used within 60 minutes of preparation. The vaccines were given in two injections of 50 µl each, on the left and right side of the abdominal mid line. OVA was used at a dose of 10 or 100 µg, and the TPCS$_{2a}$ dose was 150 µg. 18 hours after the vaccine injection, the mice were anaesthetised by intraperitoneal injection of a mixture of ketamine (25 mg/kg body weight) and xylazin (4 mg/kg) and placed on the LumiSource light source (for illumination and activation of the photosensitiser TPCS$_{2a}$). The illumination time was 6 minutes.

On day 7 thereafter mice were bled by tail bleeding and erythrocytes were removed by lysis, before analysis of antigen-specific CD8 T cells by flow cytometry. At the end of the experiment, the mice were euthanized.

Analysis of Immune Responses

The frequency of OVA-specific CD8 T-cells in blood was monitored by staining the cells with anti-CD8 antibody and H-2K$^b$/SIINFEKL Pro5 pentamer (Proimmune, Oxford, UK) for analysis by flow cytometry. The activation status of the cells was further analysed by testing the expression of CD44 by flow cytometry. The cells were analysed using FACSCanto (BD Biosciences, San Jose, USA) and analysed using FlowJo 8.5.2 software (Tree Star, Inc., Ashland, Oreg.).

GM-CSF Experiment.

The experiment was performed as described under Materials and Methods, and mouse blood samples from day 7 after vaccination were analysed by flow cytometry as described. All mice received OT-1 cells as described.

The following experimental groups were included:
1. Untreated: Mice received OT-1 cells, but were not vaccinated or illuminated.
2. OVA: Mice were vaccinated with 10 µg of OVA. They were not illuminated.
3. OVA+GM-CSF: Mice were vaccinated with a mixture of 10 µg OVA+10 µg GM-CSF. They were not illuminated.
4. OVA PCI: Mice were vaccinated with a mixture of 10 µg OVA+150 µg TPCS$_{2a}$. Illuminated as described.
5. OVA+gm-CSF PCI: Mice were vaccinated with a mixture of 10 µg OVA+10 µg gm-CSF+150 µg TPCS$_{2a}$. Illuminated as described.

FIG. 2A shows representative dot plots from the flow cytometry analysis. The population within the ellipses thus represents the CD8$^+$, pentamer$^+$, CD44$^+$ cells, representing the antigen-specific (pentamer binding), activated (CD44 expression) CD8$^+$ cells. It can be seen that the number of cells in this population is increased (as compared to the OVA group) in the OVA+GM-CSF and the OVA PCI groups), and that the effect is further significantly increased in the OVA+GM-CSF PCI group.

FIG. 2B. shows the average values (% antigen-specific, CD44$^+$ cells of the total CD8$^+$ cells) for the experimental groups, again showing a substantial increase in the OVA+GM-CSF PCI group over all the other groups.

Example 3

Effect of GM-CSF on In Vivo Vaccination with HPV

Materials and Methods
Animals

C57BL/6 mice were purchased from Harlan (Horst, The Netherlands). All mice were kept under SPF conditions, and the procedures performed were approved by the veterinary authorities in Norway.

Materials and Cells

The HPV 16 E7 peptide antigen (sequence QAEPD RAHYNIVTFCCKCDSTLRLCVQSTHVDIR, the CD8 epitope is underlined) was obtained from United Peptides (Herndon, Va.). High MW Poly(IC) was from InvivoGen (San Diego, USA). GM-CSF (recombinant murine) was purchased from PeproTech Inc., Rocky Hill, USA (Catalog#315-03). The photosensitiser tetraphenyl chlorin disulfonate (TPCS$_{2a}$) was from PCI Biotech (Lysaker, Norway), and HPV pentamer were from Proimmune (Oxford, UK), (Proimmune peptide codes 502H).

Intradermal Photosensitisation and Immunisation of Mice.

The mice were shaved on the abdominal area, and the vaccines, consisting of 50 µg HPV long peptide antigen, 100 µg TPCS$_{2a}$ and 10 µg GM-CSF and/or poly(IC) (as specified below) were injected intradermally using syringes with 29 G needles. The vaccines were kept light protected and used within 60 minutes of preparation. The vaccines were given in two injections of 50 µl each, on the left and right side of the abdominal mid line. 18 hours after immunisation the mice were anaesthetised by intraperitoneal injection of a mixture of ketamine (25 mg/kg body weight) and xylazin (4 mg/kg) and illuminated as described below.

On day 7 after each immunisation mice were bled by tail bleeding and erythrocytes were removed by lysis, before analysis of antigen-specific CD8 T cells by flow cytometry.

Illumination of Immunised Mice.

TPCS$_{2a}$ was activated by illumination with Lumi Source™ (PCI Biotech). Illumination with LumiSource was performed for 6 min, 18 hours after immunisation.

Analysis of Immune Responses by Pentamer Staining.

The frequency of antigen specific CD8 T-cells in blood was monitored by flow cytometry after staining the cells with anti-CD8 and anti-CD44 antibodies and a pentamer corresponding to the HPV antigen used. The activation status of the cells was analysed by testing the expression of CD44 by flow cytometry. The cells were analysed using FACSCanto (BD Biosciences, San Jose, USA) and analysed using FlowJo 8.5.2 software (Tree Star, Inc., Ashland, Oreg.).

Example 3a

Effect of PCI with HPV Long Peptide Antigen and GM-CSF

The experiment was performed as described under Materials and Methods. The animals were immunised at day 0 and at day 14 with vaccine mixtures as specified below. Illumination for 6 min was performed with the LumiSource illumination device, 18 hours after immunisation. Blood samples from day 6 after each immunisation were stained with HPV pentamer, CD8 and CD44 antibodies, and analysed by flow cytometry as described. The following experimental groups were included:

2×HPV: Mice were immunised 2 times with 50 µg HPV long peptide. The mice were not illuminated.

2×HPV+GM-CSF: Mice were immunised 2 times with 50 µg HPV long peptide and 10 µg GM-CSF. The mice were not illuminated.

2×HPV+GM-CSF+PCI: Mice were immunised 2 times with 50 µg HPV long peptide, 100 µg TPCS$_{2a}$ and 10 µg-GM-CSF. The mice were illuminated at both immunisations.

Results

As can be seen in FIG. 3 two immunisations with antigen+GM-CSF did not improve the immunological CD8-cell response over what was observed with antigen alone. However, combining GM-CSF with PCI substantially increased the CD8-cell response.

Example 3b

Effect of PCI with HPV Long Peptide Antigen, GM-CSF and Poly(IC)

The experiment was performed as described under Materials and Methods. The animals were immunised at day 0 and at day 14 with vaccine mixtures as specified below. Illumination for 6 min was performed with the LumiSource illumination device, 18 hours after immunisation. Blood samples from day 6 after each immunisation were stained with HPV pentamer, CD8 and CD44 antibodies, and analysed by flow cytometry as described. The following experimental groups were included:

2×HPV: Mice were immunised 2 times with 50 µg HPV long peptide. The mice were not illuminated.

2×HPV+poly(IC): Mice were immunised 2 times with 50 µg HPV long peptide and 10 µg poly(IC). The mice were not illuminated.

1$^{st}$: HPV+p(IC)+PCI. 2$^{nd}$: HPV+PCI: Mice were immunised with a mixture of 50 µg HPV long peptide, 10 µg poly(IC) and 100 µg TPCS$_{2a}$ (1$^{st}$ immunisation), and 50 µg HPV long peptide and 100 µg TPCS$_{2a}$ (2$^{nd}$ immunisation). The mice were illuminated at both immunisations.

1$^{st}$: HPV+p(IC)+GM-CSF+PCI. 2$^{nd}$: HPV+GM-CSF+PCI: Mice were immunised with a mixture of 50 µg HPV long peptide, 10 µg poly(IC), 10 µg GM-CSF and 100 µg TPCS$_{2a}$ (1$^{st}$ immunisation), and 50 µg HPV long peptide, 10 µg GM-CSF and 100 µg TPCS$_{2a}$ (2$^{nd}$ immunisation). The mice were illuminated at both immunisations.

Results

In this experiment, the first immunisation was performed with the HPV antigen alone, with antigen+poly(IC) or with combinations of the antigen+poly(IC)+PCI, or the antigen+poly(IC)+GM-CSF+PCI. The second immunisations were performed with the same combinations, but, for samples treated with PCI, without poly(IC). It can be seen from FIG. 4 that while the treatment regimen with PCI+poly(IC) alone had a positive effect on the immunological response, adding GM-CSF to the same treatment regimen substantially enhanced the response. Immunisation with antigen+GM-CSF+PCI improved the immunological CD8-cell response significantly over what was observed with antigen alone (FIG. 3), but the magnitude of the response was substantially smaller than what was observed for the combination of GM-CSF and poly(IC) and PCI (FIG. 4). Taken together with the observation that without PCI the use of poly(IC) did not improve the immunological response over what was achieved with antigen alone, the experiments indicate that when used with PCI GM-CSF and poly(IC) PCI can act synergistically to enhance the CD8 response to a peptide antigen.

The invention claimed is:

1. A method of generating an immune response in a subject, comprising administering to said subject an antigenic molecule, a photosensitizing agent, and a cytokine, and irradiating said subject with light of a wavelength effective to activate said photosensitizing agent, wherein an immune response is generated.

2. The method as claimed in claim 1 wherein said method is a method of vaccination.

3. The method as claimed in claim 1 for treating or preventing a disease, disorder or infection resulting from human papillomavirus (HPV) infection.

4. The method as claimed in claim 1 wherein said subject is a non-mammalian animal or a mammal.

5. The method as claimed in claim 1 wherein said antigenic molecule, photosensitising agent and cytokine are administered to said subject simultaneously, separately or sequentially.

6. The method of claim 1 wherein:
   a) the antigenic molecule is a molecule capable of stimulating an immune response;
   b) the cytokine is selected from GM-CSF, IL-7, IFN-α, IL-15 and IL-21; and/or
   c) the photosensitizing agent is selected from $TPCS_{2a}$, $AlPcS_{2a}$, $TPPS_4$ and $TPBS_{2a}$, or a conjugate of a photosensitiser and chitosan as defined in formula (I):

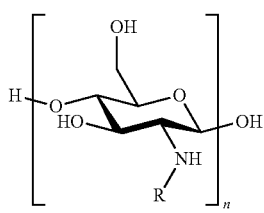

(I)

wherein
n is an integer greater than or equal to 3;
R appears n times in said compound and each R group is either a group A or group B, and
in 0.1%-99.9% of said total Rn groups, each R is a group A selected from:

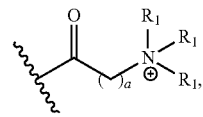

wherein each $R_1$, which may be the same or different, is selected from H, $CH_3$ and $—(CH_2)_b—CH_3$; a is 1, 2, 3, 4 or 5; and b is 0, 1, 2, 3, 4 or 5,
and

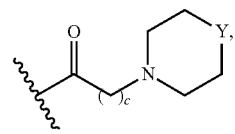

wherein Y is O; S; $SO_2$; $NCH_3$; or $—N(CH_2)_dCH_3$; c=1, 2, 3, 4 or 5; and d=1, 2, 3, 4 or 5,
wherein each R group may be the same or different, and in 0.1%-99.9% of said total Rn groups, each R is a group B selected from:

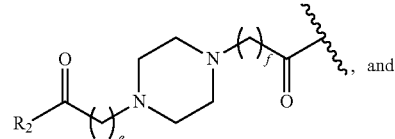, and

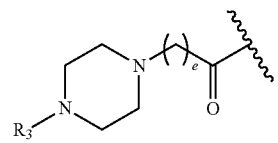

wherein e is 0, 1, 2, 3, 4 or 5; and f is 1, 2, 3, 4 or 5, $R_2$ is a group selected from:

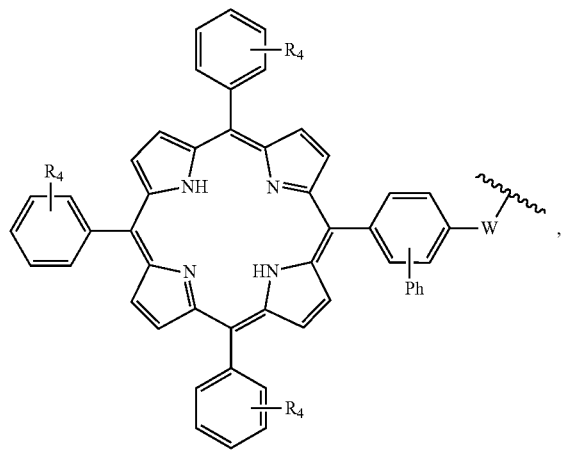

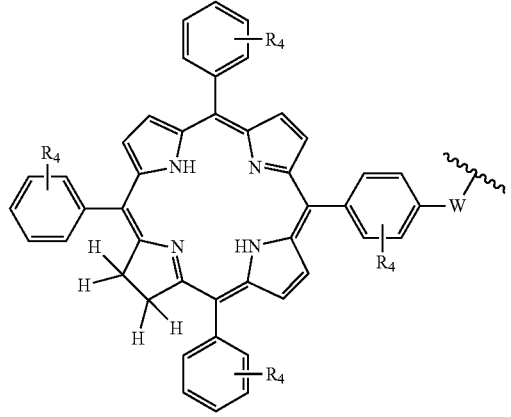

and

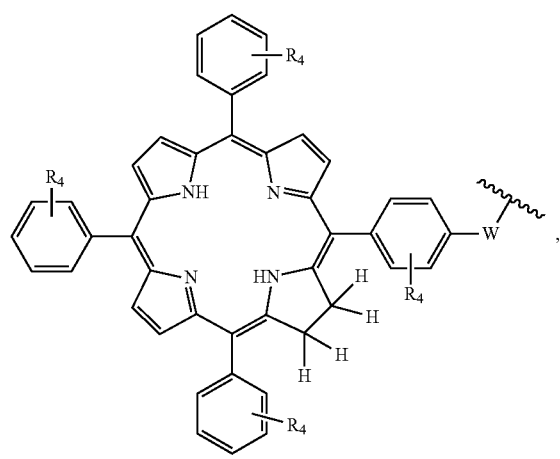

W is a group selected from O, S, NH or N(CH$_3$), $R_3$ is a group selected from:

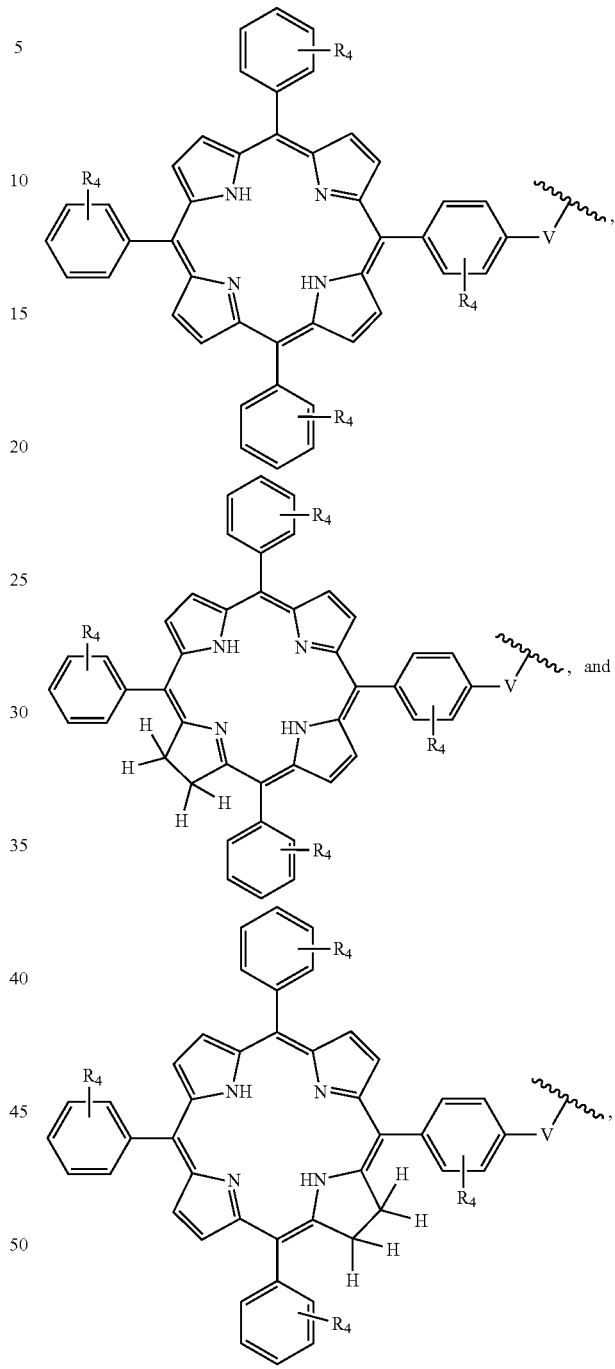

V is a group selected from CO, SO$_2$, PO, PO$_2$H or CH$_2$, and $R_4$ is a group (substituted in the o, m or p position), which may be the same or different, selected from H, —OH, —OCH$_3$, —CH$_3$, —COCH$_3$, C(CH$_3$)$_4$, —NH$_2$, —NHCH$_3$, —N(CH$_3$)$_2$ and —NCOCH$_3$, wherein each R group may be the same or different.

7. The method of claim 1, wherein upon activation of said photosensitizing agent, said antigenic molecule is released into the cytosol of a cell and the antigenic molecule or a part thereof is subsequently presented on the surface of the cell.

8. The method of claim 1, wherein the antigenic molecule is a molecule capable of stimulating an immune response.

9. The method of claim 1, wherein the antigenic molecule is a vaccine antigen or vaccine component.

10. The method of claim 1, wherein the antigenic molecule is a peptide.

11. The method of claim 1, wherein the antigenic molecule is a HPV peptide.

12. The method of claim 4, wherein said mammal is a cat, dog, horse, donkey, sheep, pig, goat, cow, mouse, rat, rabbit, guinea pig or human.

13. The method of claim 6, wherein the photosensitizing agent is $TPCS_{2a}$.

14. The method of claim 6, wherein in 0.5%-99.5% of said total Rn groups, each R is a group A as set forth in claim 6 and/or in 0.5%-99.5% of said total Rn groups, each R is a group B as set forth in claim 6.

15. The method of claim 6, wherein in said group A:

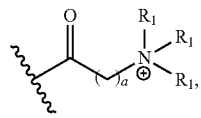

$R_1$ is $CH_3$ and b is 1;

in said group A:

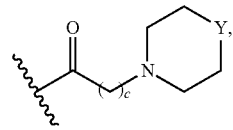

Y is $NCH_3$ and c is 1; and/or in said group B:

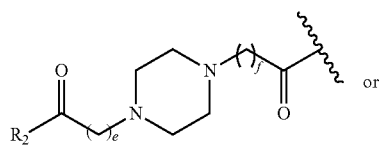

or

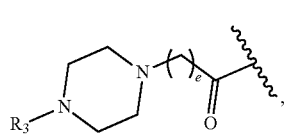

e and f=1;

$R_2$ is a group selected from:

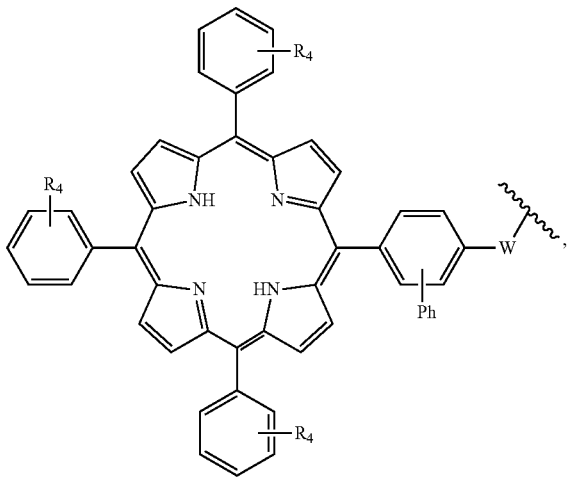

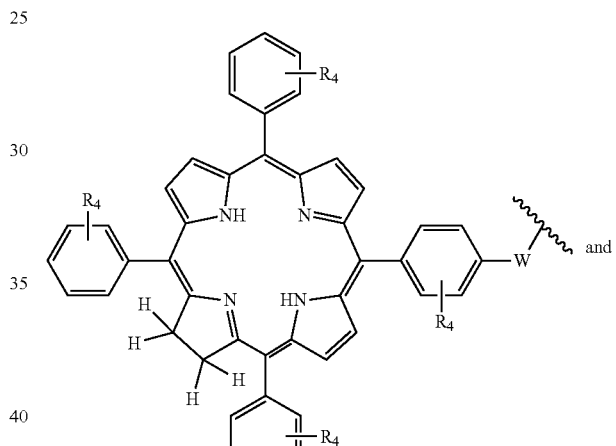

and

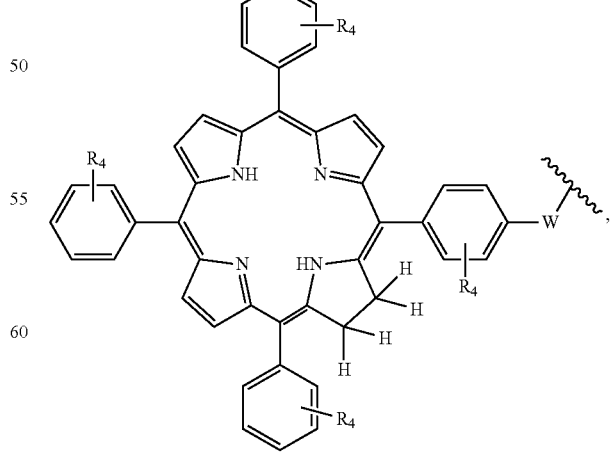

in which W is NH;

$R_3$ is a group selected from:

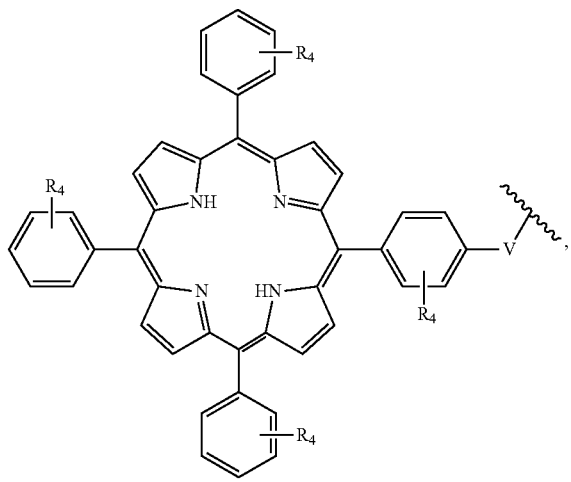

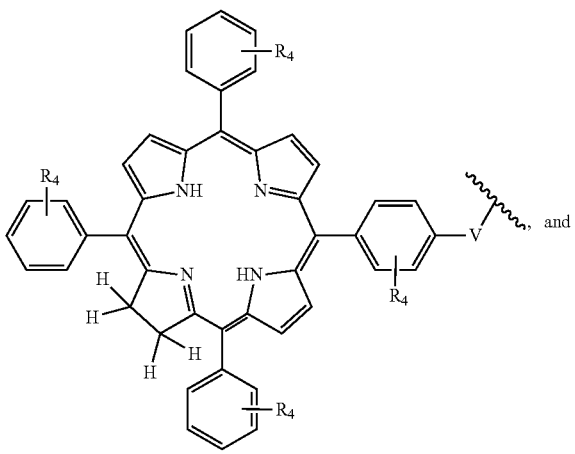, and

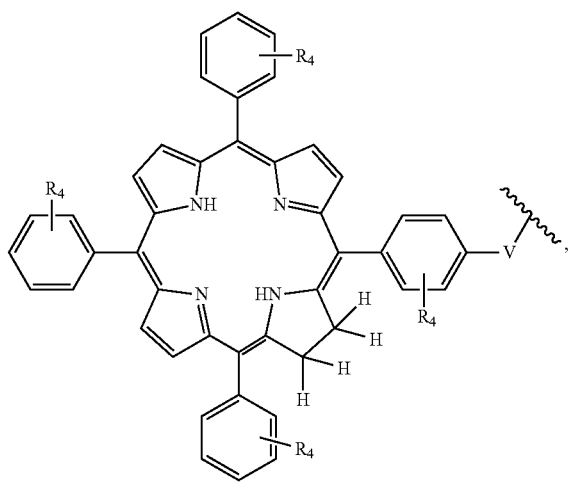

in which V is CO; and/or
$R_4$ is H.

16. The method of claim 6, wherein in said group A:

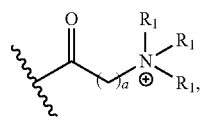

the counter-ion is Cl⁻.

17. A method of generating an immune response in a subject, comprising preparing a population of cells and subsequently administering said cells to said subject,
wherein said population of cells is prepared by contacting a population of cells with an antigenic molecule, a photosensitising agent, and a cytokine, and irradiating said cells with light of a wavelength effective to activate the photosensitising agent, whereupon said antigenic molecule is released into the cytosol of the cell and the antigenic molecule or a part thereof is subsequently presented on the surface of the cell.

18. The method of claim 17 wherein in said method of preparing a population of cells:
a) the antigenic molecule is a molecule capable of stimulating an immune response;
b) the cytokine is selected from GM-CSF, IL-7, IFN-α, IL-15 and IL-21; and/or
c) the photosensitizing agent is selected from $TPCS_{2a}$, $AlPcS_{2a}$, $TPPS_4$ and $TPBS_{2a}$, or a conjugate of a photosensitiser and chitosan as defined in formula (I):

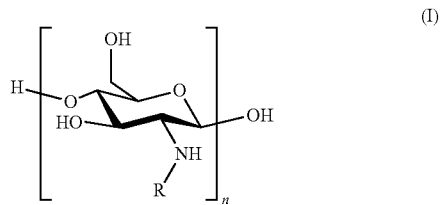

wherein
n is an integer greater than or equal to 3;
R appears n times in said compound and each R group is either a group A or group B, and
in 0.1%-99.9% of said total Rn groups, each R is a group A selected from:

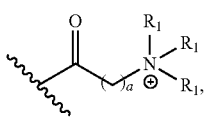

wherein each $R_1$, which may be the same or different, is selected from H, $CH_3$ and $—(CH_2)_b—CH_3$; a is 1, 2, 3, 4 or 5; and b is 0, 1, 2, 3, 4 or 5,
and

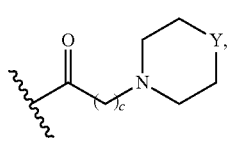

wherein Y is O; S; SO$_2$; —NCH$_3$; or —N(CH$_2$)$_d$CH$_3$; c=1, 2, 3, 4 or 5; and d=1, 2, 3, 4 or 5,
wherein each R group may be the same or different, and in 0.1%-99.9% of said total Rn groups, each R is a group B selected from:
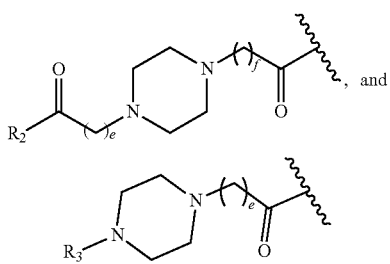, and
wherein
e is 0, 1, 2, 3, 4 or 5; and f is 1, 2, 3, 4 or 5,
R$_2$ is a group selected from:
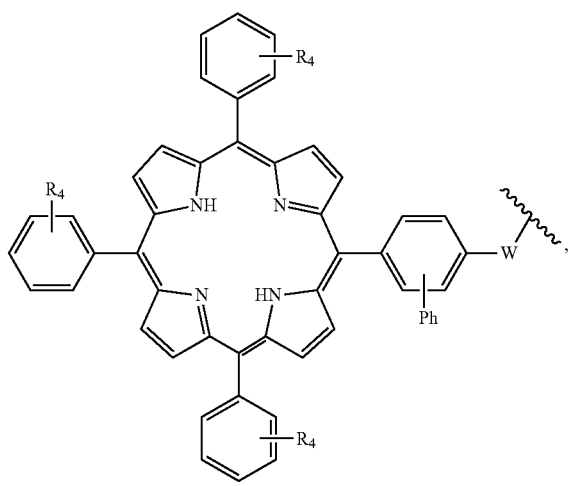,
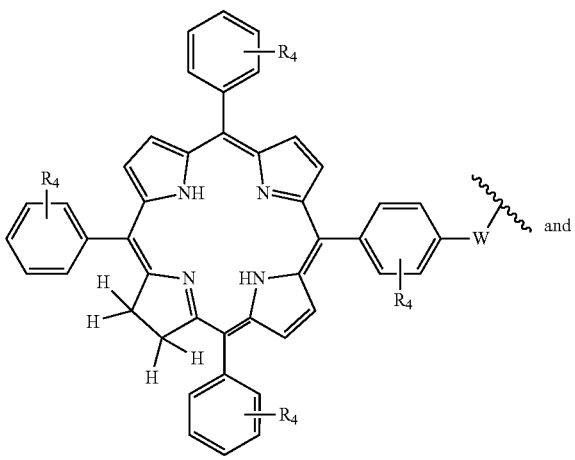, and
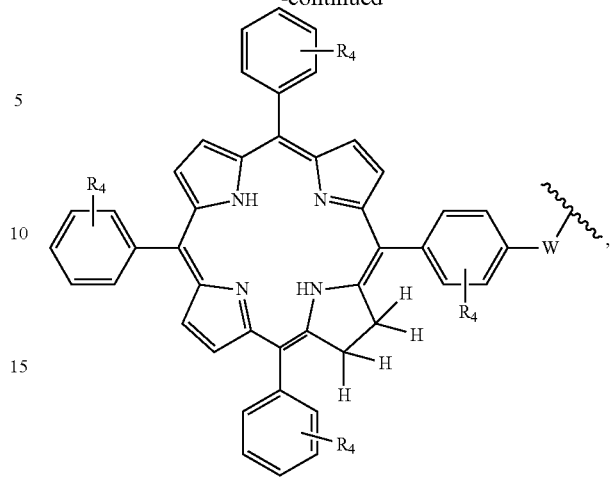,
W is a group selected from O, S, NH or N(CH$_3$),
R$_3$ is a group selected from:
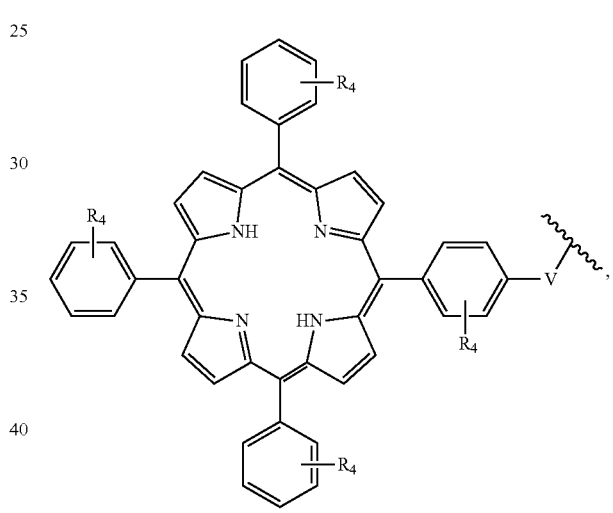,
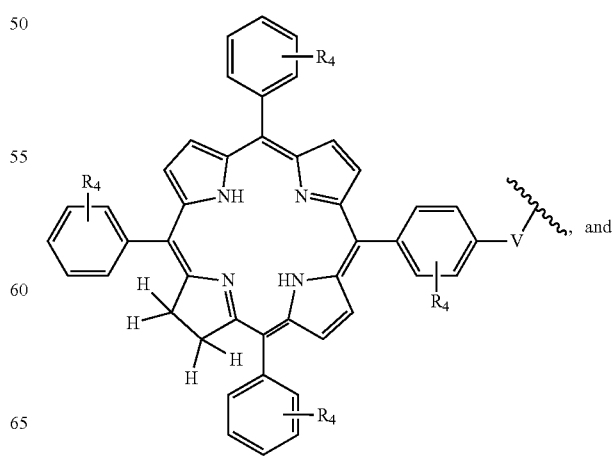, and -continued

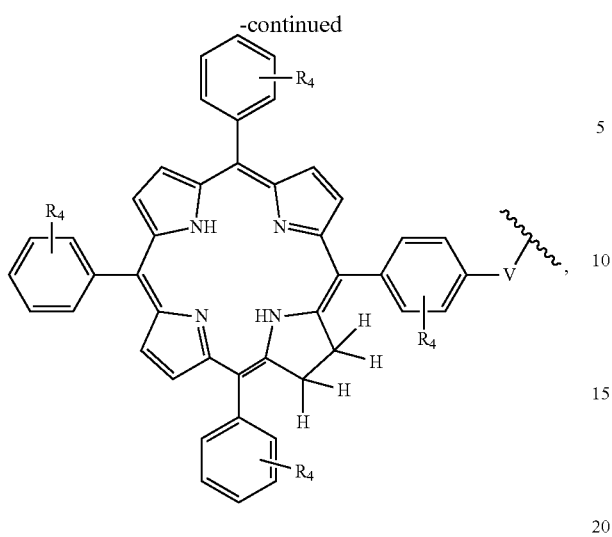

V is a group selected from CO, SO$_2$, PO, PO$_2$H or CH$_2$, and

R$_4$ is a group (substituted in the o, m or p position), which may be the same or different, selected from H, —OH, —OCH$_3$, —CH$_3$, —COCH$_3$, C(CH$_3$)$_4$, —NH$_2$, —NHCH$_3$, —N(CH$_3$)$_2$ and —NCOCH$_3$, wherein each R group may be the same or different.

19. The method of claim 17, wherein the antigenic molecule is a molecule capable of stimulating an immune response.

20. The method of claim 17, wherein the antigenic molecule is a vaccine antigen or vaccine component.

21. The method of claim 17, wherein the antigenic molecule is a peptide.

22. The method of claim 17, wherein the antigenic molecule is a HPV peptide.

23. The method of claim 17, wherein said method is a method of vaccination.

24. The method of claim 17, wherein said method is a method for treating or preventing a disease, disorder or infection resulting from HPV infection.

25. The method of claim 18, wherein the photosensitizing agent is TPCS$_{2a}$.

26. The method of claim 18, wherein in 0.5%-99.5% of said total Rn groups, each R is a group A as set forth in claim 18 and/or in 0.5%-99.5% of said total Rn groups, each R is a group B as set forth in claim 18.

27. The method of claim 18, wherein
in said group A:

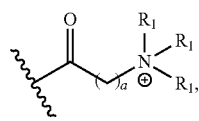

R$_1$, is CH$_3$ and b is 1;
in said group A:

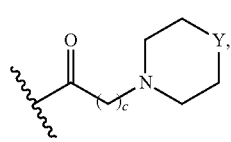

Y is NCH$_3$ and c is 1; and/or
in said group B:

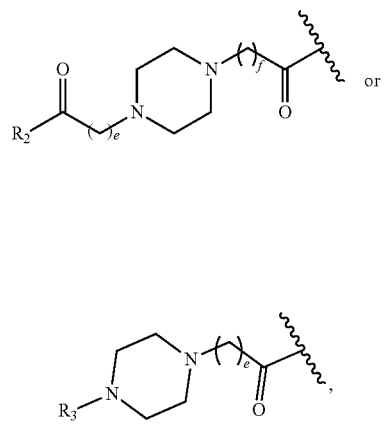

e and f=1;
R$_2$ is a group selected from:

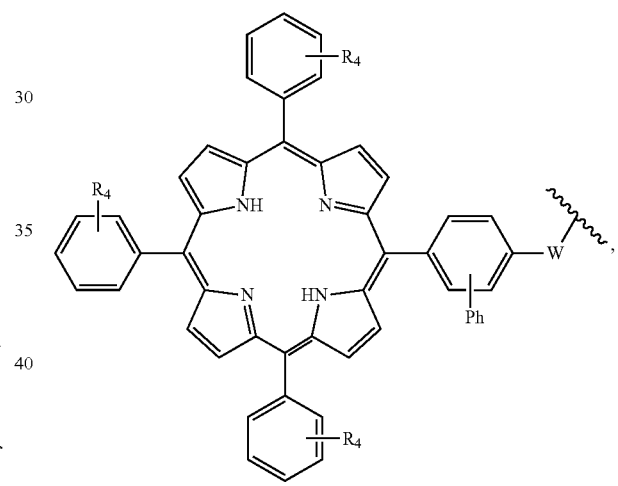

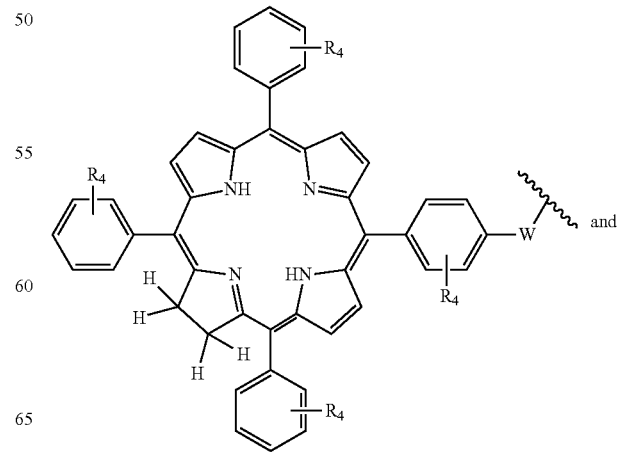

-continued
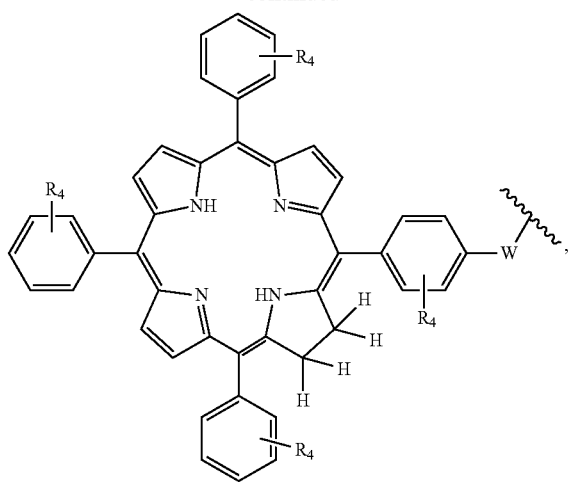
in which W is NH;
R₃ is a group selected from:
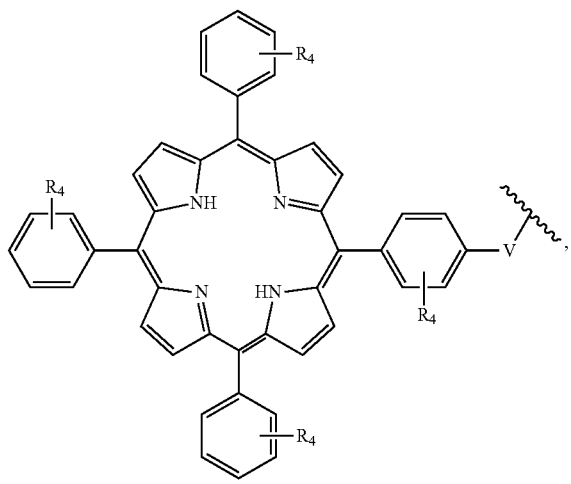
-continued
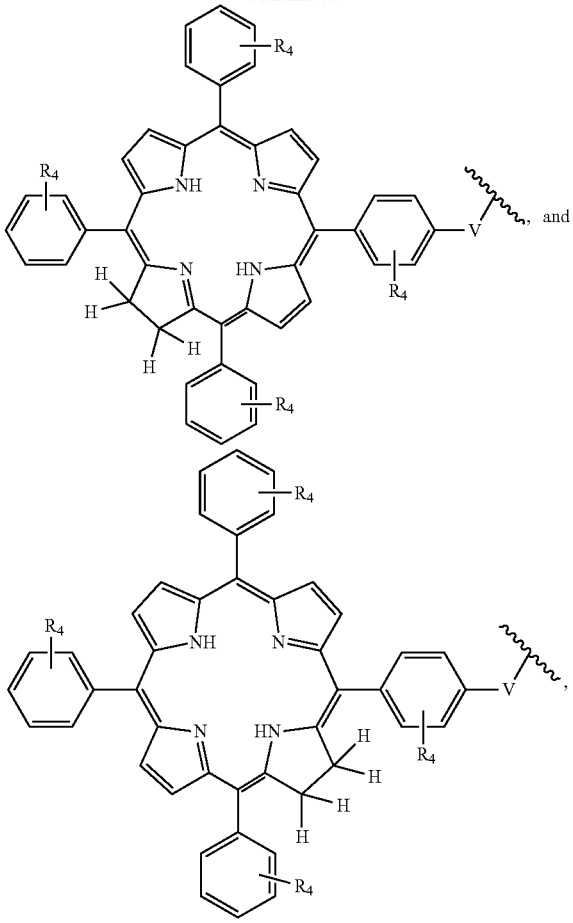
in which V is CO; and/or
R₄ is H.
28. The method of claim 18, wherein in said group A:
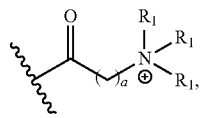
the counter-ion is Cl⁻.
* * * * *